United States Patent
Edwards et al.

(10) Patent No.: US 11,760,793 B2
(45) Date of Patent: Sep. 19, 2023

(54) ANTIBODY FOR SKEWING SEX RATIO AND METHODS OF USE THEREOF

(71) Applicant: UNIVERSITY OF TENNESSEE RESEARCH FOUNDATION, Knoxville, TN (US)

(72) Inventors: J. Lannett Edwards, Sevierville, TN (US); Louisa A. Rispoli, Maynardville, TN (US); F. Neal Schrick, Sevierville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 145 days.

(21) Appl. No.: 17/126,677

(22) Filed: Dec. 18, 2020

(65) Prior Publication Data

US 2022/0195019 A1 Jun. 23, 2022

(51) Int. Cl.
*C07K 16/18* (2006.01)
*C12N 5/076* (2010.01)
*C12N 5/071* (2010.01)

(52) U.S. Cl.
CPC .............. *C07K 16/18* (2013.01); *C12N 5/061* (2013.01); *C12N 5/0612* (2013.01)

(58) Field of Classification Search
None
See application file for complete search history.

(56) References Cited

U.S. PATENT DOCUMENTS

| | | |
|---|---|---|
| 2003/0162238 A1 | 8/2003 | Blecher et al. |
| 2005/0130115 A1 | 6/2005 | Funk et al. |
| 2009/0208977 A1 | 8/2009 | Hudson et al. |
| 2015/0233920 A1* | 8/2015 | Edwards .......... G01N 33/56966 530/388.7 |

FOREIGN PATENT DOCUMENTS

| | | |
|---|---|---|
| JP | 2006-521795 A | 9/2006 |
| JP | 2009-284799 A | 12/2009 |
| JP | 2010-268796 A | 12/2010 |
| WO | 2004-083362 A2 | 9/2004 |
| WO | 2008067651 A1 | 6/2008 |
| WO | 2010120518 A2 | 10/2010 |
| WO | 2010150013 A2 | 12/2010 |
| WO | 2015127055 A1 | 8/2015 |

OTHER PUBLICATIONS

Kussie "A Single Engineered Amino Acid Substitution Changes Antibody Fine Specificity" J immunol 152(1):146-52 (Year: 1994).*
English machine translation of JP 2006-521795 Abstract.
English machine translation of JP 2010-268796 Abstract.
English machine translation of JP 2009-284799 Abstract.

* cited by examiner

*Primary Examiner* — Adam Weidner
(74) *Attorney, Agent, or Firm* — Patrick M. Torre; Stites & Harbison PLLC

(57) ABSTRACT

A purified antibody, or an antigen-binding fragment thereof, is provided that binds selectively to a protein specific to an X-chromosome of a mammalian sperm cell. The sperm cell protein includes an amino acid sequence set forth in SEQ ID NOs: 4 and 9-16. The antibody or antigen-binding fragment thereof may be derived by immunization of a host by an antigenic peptide composition including one or more natural or synthetic antigenic peptide sequences set forth as SEQ ID NO: 1, SEQ ID NO: 2, SEQ ID NO: 3, and SEQ ID NOs: 4 and 9-16. The antibody finds utility in identifying an X-chromosome bearing sperm cell population, and in methods for skewing a sex ratio in mammals. Embodiments of the subject antibodies referred to herein as anti-GX1-E protein antibody and anti-GX1-M protein antibody have the ATCC Patent Deposit Designations PTA-125897 and PTA-125898, having been deposited on Apr. 2, 2019.

13 Claims, 13 Drawing Sheets
Specification includes a Sequence Listing.

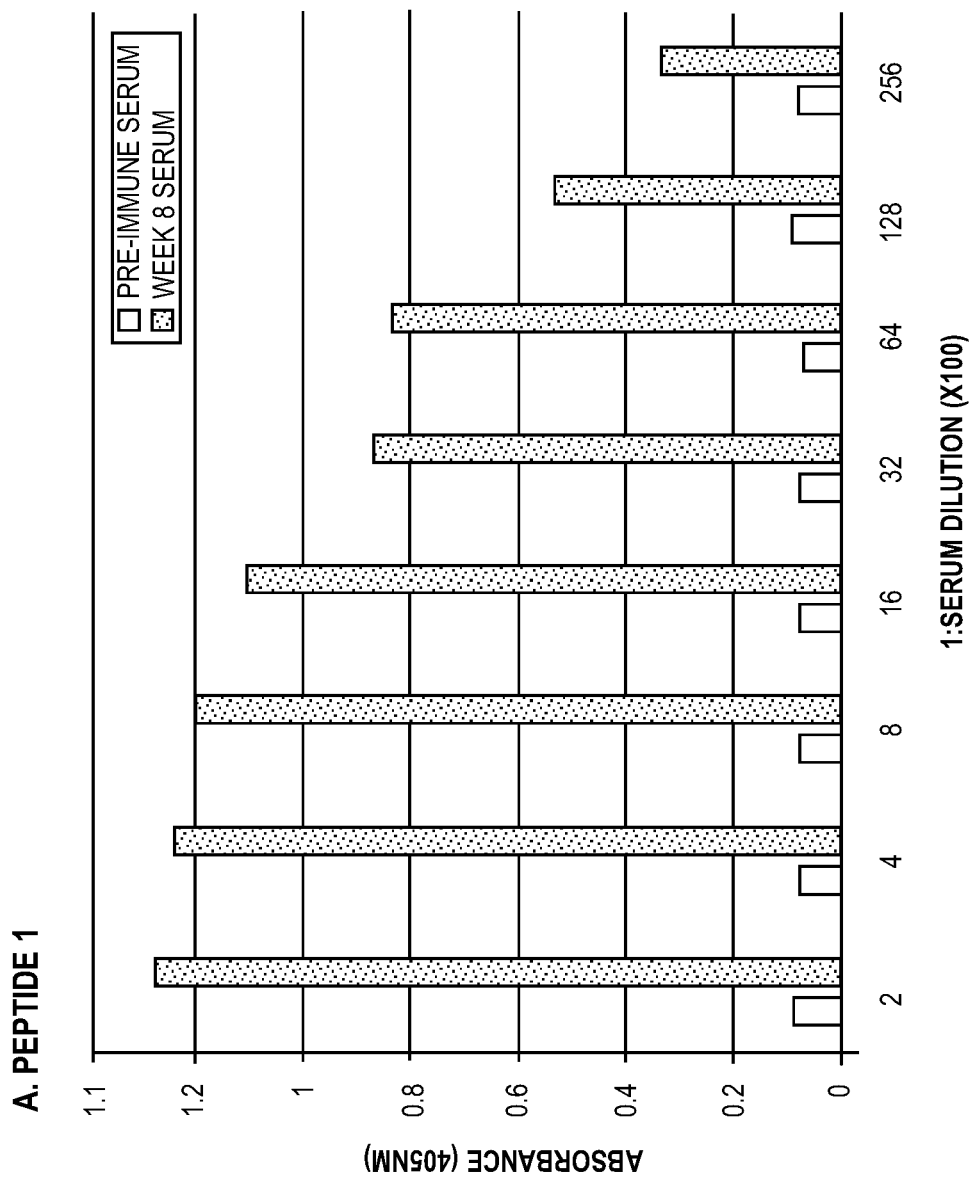

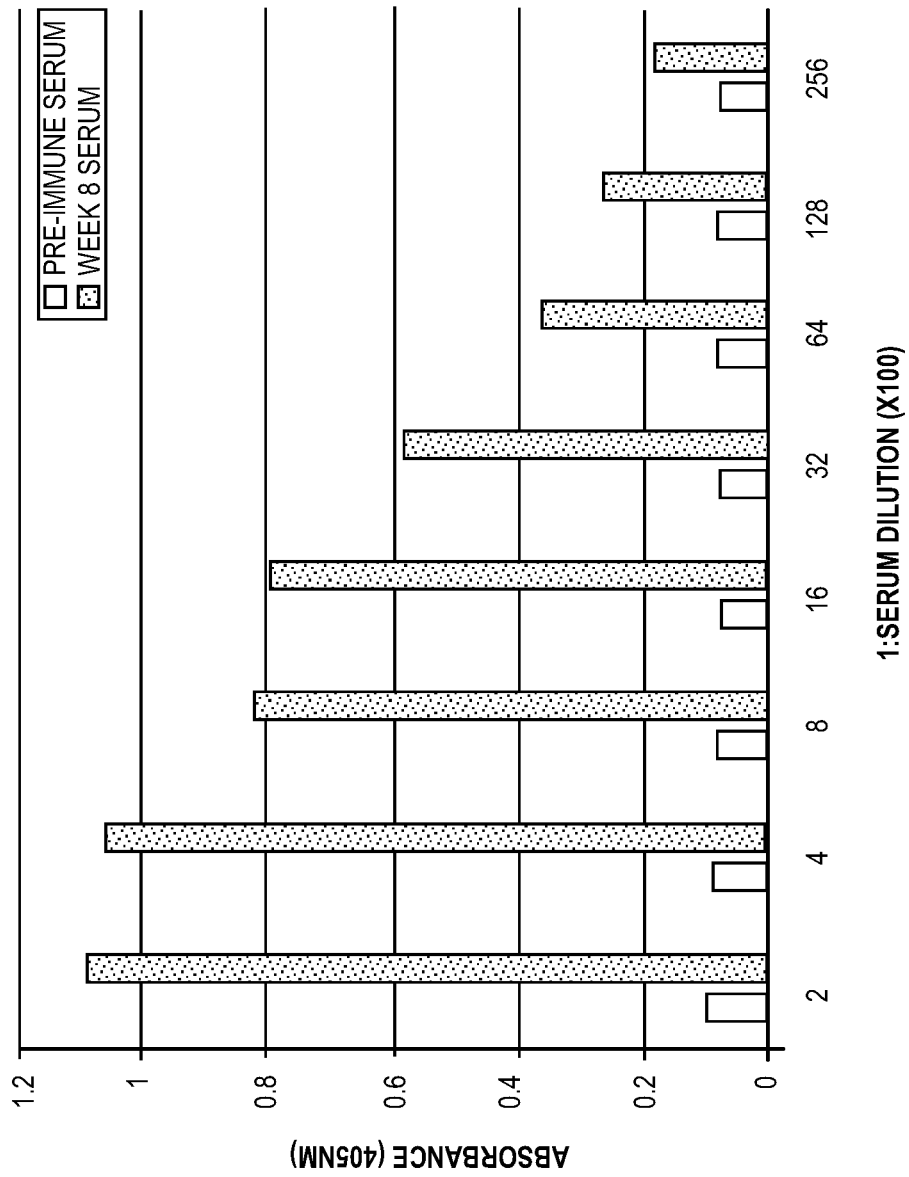

FIG 4A
FIG 4B
A. Cy2 negative sorted sperm
B. Cy2 positive sorted sperm
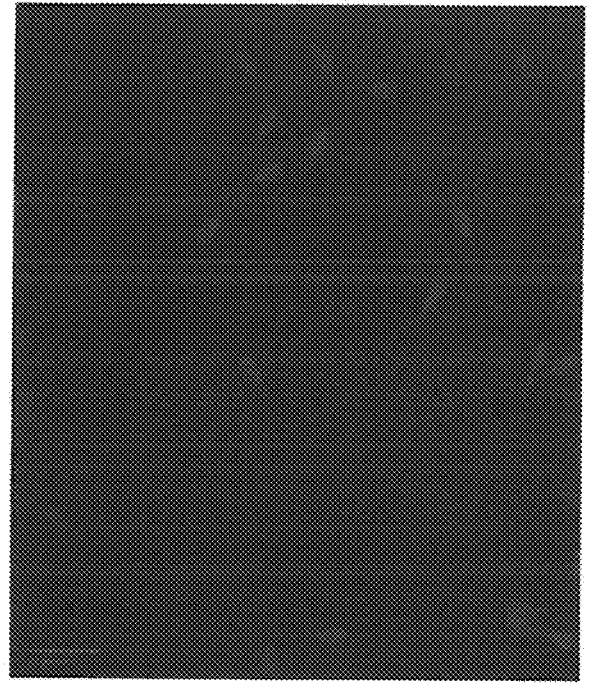
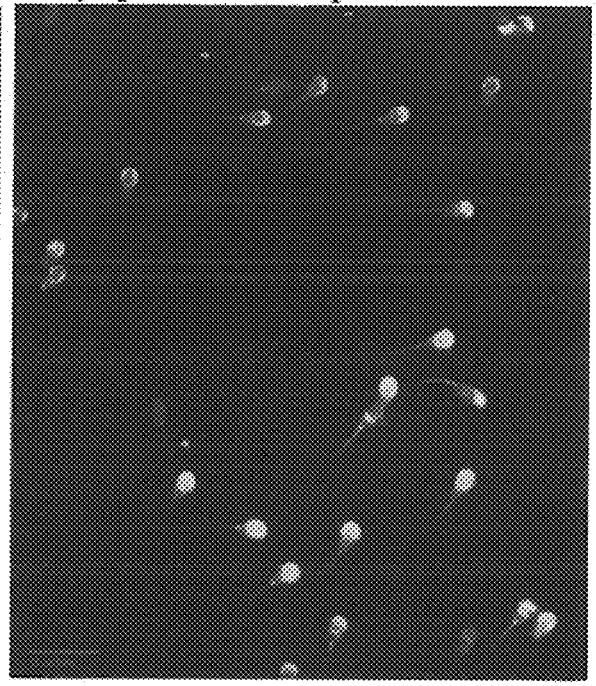

```
MTKRTGKPQG SRVVRKHLPP VTRDKRMKTS SQLRPPKNVK VARASARVEN
HLRAKLTKKT SQKPPTTRNL RKNGGSKLCS QCCKVNEELN QNGPEEVPES
VEIPVIPAGP VGSQ
```

FIG 7 (SEQ ID NO: 4)

```
MTKRTGKPQG SRVVRKHLPP VTRDKRMKTS SQLRPPKNVK VARASARVNN
HLRAKLTKKT SQKPPTTRML RKMGGSKLCS QCCKVNEELN QMGPEEVPES
VEIPVIPAGP VGSQ
```

FIG 11 (SEQ ID NO: 4)

SEQUENCE LISTING

<160> NUMBER OF SEQ ID NOS: 27

<210> SEQ ID NO 1
<211> LENGTH: 20
<212> TYPE: PRT
<213> ORGANISM: Artificial Sequence
<220> FEATURE:
<223> OTHER INFORMATION: Synthesized immunograde peptide

<400> SEQUENCE: 1

```
Cys Thr Lys Arg Thr Gly Lys Pro Gln Gly Ser Arg Val Val Arg Lys
1               5                   10                  15

His Leu Pro Pro
            20
```

<210> SEQ ID NO 2
<211> LENGTH: 21
<212> TYPE: PRT
<213> ORGANISM: Artificial Sequence
<220> FEATURE:
<223> OTHER INFORMATION: Synthesized immunograde peptide

<400> SEQUENCE: 2

```
Cys Lys Thr Ser Ser Gln Leu Arg Pro Pro Lys Asn Val Lys Val Ala
1               5                   10                  15

Arg Ala Ser Ala Arg
            20
```

<210> SEQ ID NO 3
<211> LENGTH: 20
<212> TYPE: PRT
<213> ORGANISM: Artificial Sequence
<220> FEATURE:
<223> OTHER INFORMATION: Synthesized immunograde peptide

<400> SEQUENCE: 3

```
Cys Lys Val Asn Glu Glu Leu Asn Gln Asn Gly Pro Glu Glu Val Pro
1               5                   10                  15

Glu Ser Val Glu
            20
```

<210> SEQ ID NO 4
<211> LENGTH: 114
<212> TYPE: PRT
<213> ORGANISM: Bos taurus

<400> SEQUENCE: 4

```
Met Thr Lys Arg Thr Gly Lys Pro Gln Gly Ser Arg Val Val Arg Lys
1               5                   10                  15

His Leu Pro Pro Val Thr Arg Asp Lys Arg Met Lys Thr Ser Ser Gln
            20                  25                  30

Leu Arg Pro Pro Lys Asn Val Lys Val Ala Arg Ala Ser Ala Arg Val
        35                  40                  45

Asn Asn His Leu Arg Ala Lys Leu Thr Lys Lys Thr Ser Gln Lys Pro
    50                  55                  60

Pro Thr Thr Arg Asn Leu Arg Lys Asn Gly Gly Ser Lys Leu Cys Ser
65                  70                  75                  80

Gln Cys Cys Lys Val Asn Glu Glu Leu Asn Gln Asn Gly Pro Glu Glu
                85                  90                  95

Val Pro Glu Ser Val Glu Ile Pro Val Ile Pro Ala Gly Pro Val Gly
            100                 105                 110
```

Ser Gln

<210> SEQ ID NO 5
<211> LENGTH: 563
<212> TYPE: DNA
<213> ORGANISM: Bos taurus

<400> SEQUENCE: 5

```
atgagggtgt gtctccctgg ggaggggtat atatagcggt gctcaggggc tctggagcag      60
accactggga ggcctcaaaa tgactaagcg gactgggaag ccccaaggct ccagagtagt     120
taggaaacac ctgcctcctg ttacccggga caaaaggatg aagacctcct ctcaactgag     180
gcccccaaaa aatgtcaagg tggccagggc aagtgcgaga gtgaataatc accttcgggc     240
aaagctgacc aagaaaactt ctcagaaacc acccaccaca aggaacctta gaaaaaacgg     300
aggctcaaag ctctgtagcc agtgttgcaa ggtgaatgaa gagctgaatc agaacggacc     360
agaggaggtc ccagagagtg tggagatccc tgtcattcca gcgggaccgg tgggcagcca     420
gtgacttgaa ggcatggctc gagacctcag aattcttcgg gggtcttgcc gctgagtact     480
ggccaacagt acagacgtga ctattatacc aactccatac attaagaatg aaagaaaat      540
aaaatcaacc tgatgtgaaa tta                                             563
```

<210> SEQ ID NO 6
<211> LENGTH: 24
<212> TYPE: DNA
<213> ORGANISM: Artificial Sequence
<220> FEATURE:
<223> OTHER INFORMATION: qPCR primer 1

<400> SEQUENCE: 6

```
aagcatgagg gtgtgtctcc ctgg                                             24
```

<210> SEQ ID NO 7
<211> LENGTH: 23
<212> TYPE: DNA
<213> ORGANISM: Artificial Sequence
<220> FEATURE:
<223> OTHER INFORMATION: qPCR primer 2

<400> SEQUENCE: 7

```
tcctaactac tctggagcct tgg                                              23
```

<210> SEQ ID NO 8
<211> LENGTH: 14
<212> TYPE: DNA
<213> ORGANISM: Artificial Sequence
<220> FEATURE:
<223> OTHER INFORMATION: nucleic acid probe

<400> SEQUENCE: 8

```
agccctgtgc cctg                                                        14
```

<210> SEQ ID NO 9
<211> LENGTH: 114
<212> TYPE: PRT
<213> ORGANISM: Bos taurus

<400> SEQUENCE: 9

```
Met Thr Lys Arg Thr Gly Lys Pro Gln Gly Ser Arg Val Val Arg Lys
1               5                   10                  15

His Leu Pro Pro Val Thr Arg Asp Lys Arg Met Lys Thr Ser Ser Gln
            20                  25                  30
```

```
Leu Arg Pro Pro Lys Asn Val Lys Val Ala Arg Ala Ser Ala Arg Val
            35                  40                  45

Asn Asn His Leu Gln Ala Lys Leu Thr Lys Thr Ser Gln Lys Pro
 50                  55                  60

Pro Thr Thr Arg Asn Leu Ser Lys Asn Gly Gly Ser Lys Leu Cys Ser
 65                  70                  75                  80

Gln Cys Cys Lys Val Asn Glu Glu Leu Asn Gln Asn Gly Pro Glu Glu
                    85                  90                  95

Val Pro Glu Ser Val Glu Ile Pro Val Ile Pro Ala Gly Pro Val Gly
                100                 105                 110

Ser Gln

<210> SEQ ID NO 10
<211> LENGTH: 114
<212> TYPE: PRT
<213> ORGANISM: Bos taurus

<400> SEQUENCE: 10

Met Thr Lys Arg Thr Gly Lys Pro Gln Gly Ser Arg Val Val Arg Lys
 1               5                  10                  15

His Leu Pro Pro Val Thr Arg Gly Lys Arg Met Lys Thr Ser Ser Gln
                20                  25                  30

Leu Arg Pro Lys Thr Asn Val Lys Val Ala Lys Ala Ser Ala Arg Val
            35                  40                  45

Asn Asn His Leu Gln Ala Lys Leu Thr Lys Thr Ser Gln Lys Pro
 50                  55                  60

Pro Thr Thr Arg Asn Leu Arg Lys Ile Gly Gly Ser Lys Leu Cys Ser
 65                  70                  75                  80

Gln Gly Ser Lys Val Asn Glu Glu Leu Asn Gln Asn Gly Pro Glu Glu
                    85                  90                  95

Val Pro Glu Ser Val Glu Thr Pro Val Ile Pro Ala Gly Pro Val Gly
                100                 105                 110

Ser Gln

<210> SEQ ID NO 11
<211> LENGTH: 114
<212> TYPE: PRT
<213> ORGANISM: Bos taurus

<400> SEQUENCE: 11

Met Thr Lys Arg Thr Gly Lys Pro Gln Gly Ser Arg Val Val Arg Lys
 1               5                  10                  15

His Leu Pro Pro Val Thr Arg Gly Lys Arg Met Lys Thr Ser Ser Gln
                20                  25                  30

Leu Arg Ala Lys Thr Asn Val Lys Val Ala Lys Ala Ser Ala Arg Val
            35                  40                  45

Asn Asn His Leu Gln Ala Lys Leu Thr Lys Thr Ser Gln Lys Pro
 50                  55                  60

Pro Thr Thr Arg Asn Leu Arg Lys Ile Gly Gly Ser Lys Leu Cys Ser
 65                  70                  75                  80

Gln Gly Ser Lys Val Asn Glu Glu Leu Asn Gln Asn Gly Pro Glu Glu
                    85                  90                  95

Val Pro Glu Ser Val Glu Met Pro Val Ile Pro Ala Gly Pro Val Gly
                100                 105                 110

Ser Gln
```

<210> SEQ ID NO 12
<211> LENGTH: 114
<212> TYPE: PRT
<213> ORGANISM: Bos taurus

<400> SEQUENCE: 12

Met Thr Lys Arg Thr Gly Lys Pro Gln Gly Ser Arg Val Val Arg Lys
1               5                   10                  15

His Leu Pro Arg Phe Thr Arg Asp Lys Arg Met Lys Thr Ser Ser Gln
            20                  25                  30

Leu Arg Pro Lys Thr Asn Val Lys Val Ala Arg Ala Ser Ala Arg Val
        35                  40                  45

Asn Asn His Leu Gln Ala Lys Leu Thr Lys Lys Thr Ser Gln Lys Pro
    50                  55                  60

Pro Thr Thr Arg Asn Leu Arg Lys Ile Arg Gly Ser Lys Leu Cys Ser
65                  70                  75                  80

Gln Cys Ser Lys Val Asn Glu Val Leu Asn Gln Asn Gly Pro Glu Glu
                85                  90                  95

Val Pro Glu Ser Val Glu Met Pro Val Ile Pro Val Gly Pro Val Gly
            100                 105                 110

Ser Gln

<210> SEQ ID NO 13
<211> LENGTH: 114
<212> TYPE: PRT
<213> ORGANISM: Pantholops hodgsonii

<400> SEQUENCE: 13

Met Thr Lys Val Thr Gly Lys Gln Gln Gly Ser Arg Val Val Met Lys
1               5                   10                  15

His Leu Ala Pro Val Thr Trp Asn Lys Arg Met Lys Thr Ser Ser Gln
            20                  25                  30

Leu Arg Ser Lys Lys Asn Val Lys Val Ala Arg Val Pro Val Arg Val
        35                  40                  45

Asn Asn His Leu Gln Ala Lys Leu Thr Lys Lys Thr Ser Gln Lys Pro
    50                  55                  60

Pro Thr Thr Arg Lys Leu Lys Lys Ile Arg Gly Pro Lys Leu Cys Ser
65                  70                  75                  80

Arg Cys Ser Lys Val Asn Glu Lys Leu Asn Gln Asn Gly Pro Glu Glu
                85                  90                  95

Val Pro Glu Ser Val Glu Thr Pro Val Ile Pro Ala Gly Thr Val Gly
            100                 105                 110

Ser Gln

<210> SEQ ID NO 14
<211> LENGTH: 114
<212> TYPE: PRT
<213> ORGANISM: Pantholops hodgsonii

<400> SEQUENCE: 14

Met Thr Lys Val Thr Gly Lys Pro Gln Gly Ser Arg Val Val Met Lys
1               5                   10                  15

His Leu Pro Pro Val Thr Trp Asp Asn Arg Met Lys Thr Ser Ser Gln
            20                  25                  30

Leu Arg Ser Lys Lys Asn Val Lys Val Ala Arg Val Pro Val Arg Val
        35                  40                  45

Asp Asn His Leu Gln Ala Lys Leu Thr Lys Lys Thr Ser Gln Lys Pro
            50                  55                  60

Pro Thr Thr Arg Lys Leu Lys Lys Ile Arg Gly Pro Lys Leu Cys Ser
65                  70                  75                  80

Trp Cys Ser Lys Val Asn Glu Glu Leu Asn Gln Asn Gly Pro Glu Glu
                    85                  90                  95

Val Pro Glu Ile Leu Gln Thr Pro Val Ile Pro Ala Gly Thr Val Gly
                100                 105                 110

Arg Gln

<210> SEQ ID NO 15
<211> LENGTH: 119
<212> TYPE: PRT
<213> ORGANISM: Bos taurus

<400> SEQUENCE: 15

Met Thr Lys Val Thr Gly Lys Pro Gln Gly Ser Arg Val Val Arg Lys
1               5                   10                  15

His Leu Pro Pro Val Thr Gln Asp Lys Arg Met Glu Thr Ser Ser Gln
                20                  25                  30

Leu Arg Ser Lys Lys His Val Lys Val Ala Arg Val Ser Val Arg Val
            35                  40                  45

Asn Asn His Leu Gln Ala Lys Met Thr Lys Lys Thr Ser Gln Lys Pro
        50                  55                  60

Pro Thr Thr Arg Asn Leu Arg Lys Ile Arg Gly Ser Lys Leu Cys Ser
65                  70                  75                  80

Gln Cys Ser Lys Val Asn Glu Glu Leu Asn Gln Asn Gly Pro Val Glu
                85                  90                  95

Val Pro Asp Cys Gly His Pro Cys His Ser Ser Gly Thr Gly Trp Gln
                100                 105                 110

Pro Val Thr Ser Arg His Gly
            115

<210> SEQ ID NO 16
<211> LENGTH: 93
<212> TYPE: PRT
<213> ORGANISM: Bos taurus

<400> SEQUENCE: 16

Met Glu Thr Ser Ser Gln Leu Arg Ser Lys Lys His Val Lys Val Ala
1               5                   10                  15

Arg Val Ser Val Arg Val Asn Asn His Leu Gln Ala Lys Met Thr Lys
                20                  25                  30

Lys Thr Ser Gln Lys Pro Pro Thr Thr Arg Asn Leu Arg Lys Ile Arg
            35                  40                  45

Gly Ser Lys Leu Cys Ser Gln Cys Ser Lys Val Asn Glu Glu Leu Asn
        50                  55                  60

Gln Asn Gly Pro Val Glu Val Pro Asp Cys Gly His Pro Cys His Ser
65                  70                  75                  80

Ser Gly Thr Gly Trp Gln Pro Val Thr Ser Arg His Gly
                85                  90

<210> SEQ ID NO 17
<211> LENGTH: 607
<212> TYPE: DNA
<213> ORGANISM: Bos taurus

<400> SEQUENCE: 17

```
acccagggcc accattggct gggcaggaga cttgctgacc tcataaagca tgagggtgtg      60
tctccctggg gaggggtata tatagcggtg ctcaggggct ctggagcaga ccactgggag     120
gcctcaaaat gactaagcgg actgggaagc cccaaggctc cagagtagtt aggaaacacc     180
tgcctcctgt tacccgggac aaaaggatga agacctcctc tcaactgagg cccccaaaaa     240
atgtcaaggt ggccagggca agtgcgagag tgaataatca ccttcaggca aagctgacca     300
agaaaacttc tcagaaacca cccaccacaa ggaaccttag caaaaacgga ggctcaaagc     360
tctgtagcca gtgttgcaag gtgaatgaag agctgaatca gaacggacca gaggaggtcc     420
cagagagtgt ggagatccct gtcattccag cgggaccggt gggcagccag tgacttgaag     480
gcatggctag agacctcaga attcttcggg ggtcttgccg ctgagtactg gccaacagta     540
cagacgtgac tattatacca actccataca ttaagaatga aaataaaatc aacctgatgt     600
gaaatta                                                                607
```

<210> SEQ ID NO 18
<211> LENGTH: 415
<212> TYPE: DNA
<213> ORGANISM: Bos taurus

<400> SEQUENCE: 18

```
atatagcggt gctcacgggc tctggagcag accactggga ggcctcaaaa tgactaagcg      60
gactgggaag ccccaaggct ccagagtagt taggaaacac ctgcctcctg ttacccgggg     120
caaaaggatg aagacctcct ctcaattgag gcccaaaaca aatgtcaagg tggccaaggc     180
aagtgcgaga gtgaataatc acctacaggc aaagctgacc aagaaaactt ctcagaaacc     240
gcccaccacg gaaccttag aaaaatcgg aggctcaaag ctctgtagcc agggttccaa     300
ggtgaatgaa gagctgaatc agaacggacc agaggaggtc ccagagagtg tggagatgcc     360
tgtcattcca gcgggaccgg tgggcagcca gtgacttgaa ggtatggcta gagac          415
```

<210> SEQ ID NO 19
<211> LENGTH: 666
<212> TYPE: DNA
<213> ORGANISM: Bos taurus

<400> SEQUENCE: 19

```
ctgaattgct ccccatcccc cgctagaggt gtcaggatgg ggctttgtga tgtcaaggcc      60
cacccagggc caccattggc tgggcaggag acttgctgac tcataaagc atgagggtgt     120
gtctccctgg ggaggggtat atatagcggt gctcaggggc tctggagcag accactggga     180
ggcctcaaaa tgactaagcg gactgggaag ccccaaggct ccagagtagt taggaaacac     240
ctgcctcctg ttacccgggg caaaaggatg aagacctcct ctcaattgag gccaaaaca     300
aatgtcaagg tggccaaggc aagtgcgaga gtgaataatc acctacaggc aaagctgacc     360
aagaaaactt ctcagaaacc gcccaccacg gaaccttaa aaaaatcgg aggctcaaaa     420
ctctgtagcc agggttccaa ggtgaatgaa gagctgaatc agaacggacc agaggaggtc     480
ccagagagtg tggagatgcc tgtcattcca gcgggaccgg tgggcagcca gtgacttgaa     540
ggtatggcta gagacctcag aaatctttgg gggtcttgcc actgagtact ggccaacagt     600
acagacattg actattatac caactgcata cattaagaat gaaaataaaa tcaacctgat     660
gtgaaa                                                                 666
```

<210> SEQ ID NO 20
<211> LENGTH: 1080
<212> TYPE: DNA
<213> ORGANISM: Bos taurus

<400> SEQUENCE: 20

| | | | | | |
|---|---|---|---|---|---|
| atctaaatca | gtgaaacaaa | gtattcactg | caaggaacaa | actttttta | gcttgaaaaa | 60 |
| aacaaaatcc | tcttatattt | gaacataaaa | tgtcttgctg | aatttgaaaa | ataggtttga | 120 |
| aatgaaattc | attcttgatt | gtcagttatt | ttgagactat | ggaaaacggt | cttatgttag | 180 |
| agaaaataaa | cttatgttaa | ctggggctgc | ttaagctgta | tcttttgcag | attttttttt | 240 |
| aattccctta | cattttaca | gtcataaata | gatataatag | acaaggtttg | gaggagacac | 300 |
| actctccctg | ccatgtgacc | catcagagtt | gacttagaga | gatgaggatg | gcagggagtt | 360 |
| tgaaggcctc | tttaggggaa | ttacaaatgc | cccatttctc | ccaccaaaac | atctgaattg | 420 |
| ctccccatcc | tccgctagag | gtgtcagggt | ggggctttgt | gatgtcaagg | ctcacccagg | 480 |
| gccaccattg | gctgggcagg | agacttgctg | acctcataaa | gcatgagggt | gtgtctccct | 540 |
| ggggaggggt | atatatagcg | gtgctcaggg | gctctggagc | agaccactgg | gaggcctcaa | 600 |
| aatgactaag | cggactggga | agccccaagg | ctccagagta | gttaggaaac | acctgccacg | 660 |
| ttttacccgg | gacaaaagga | tgaagacctc | ctctcaactg | aggcccaaaa | caaatgtcaa | 720 |
| ggtggccagg | gcaagtgcga | gagtgaataa | tcaccttcag | gcaaagctga | ccaagaaaac | 780 |
| ttctcagaaa | ccgcccacca | caaggaacct | tagaaaaatc | agaggctcaa | agctctgtag | 840 |
| ccagtgttcc | aaggtgaatg | aagtgctcaa | tcagaacgga | ccagaggagg | tcccagagag | 900 |
| tgtggagatg | cctgtcattc | cagtgggacc | ggtgggcagc | cagtgacttg | aaggcatggc | 960 |
| tagagacctc | agaaatcttc | ggggtcttgc | cgctgaatac | tgtccaacag | tacagacgtt | 1020 |
| gactattata | ccaactccat | acattaagaa | tgaaaataaa | atcaacctga | tgtgaaagta | 1080 |

<210> SEQ ID NO 21
<211> LENGTH: 498
<212> TYPE: DNA
<213> ORGANISM: Pantholops hodgsonii

<400> SEQUENCE: 21

| | | | | | |
|---|---|---|---|---|---|
| accactggga | ggcctcaaaa | tgactaaggt | gactgggaag | caacaaggct | ccagagtagt | 60 |
| tatgaaacac | ctggctcctg | ttacctggaa | caaaaggatg | aagacttcct | ctcaactgag | 120 |
| gtccaagaaa | aatgtcaagg | tggccagggt | acctgtgaga | gtgaataatc | accttcaggc | 180 |
| aaagctgacc | aagaaaactt | ctcagaaacc | acccaccaca | aggaaactta | aaaaaatcag | 240 |
| aggcccaaag | ctctgtagcc | ggtgctccaa | ggtgaatgaa | agctgaatc | agaatggacc | 300 |
| agaggaggtc | ccagagagtg | tggagacccc | tgtcattcca | gcaggaacag | tgggcagcca | 360 |
| gtgacctcaa | agcatggcta | gagacctcag | aaatgttcag | gggtcttgcc | gcttagtact | 420 |
| ggtcaatagt | acagacgttg | actattatac | caactgcata | cattcataat | gaaaataaaa | 480 |
| tcaacctgat | gtgaaatt | | | | | 498 |

<210> SEQ ID NO 22
<211> LENGTH: 500
<212> TYPE: DNA
<213> ORGANISM: Pantholops hodgsonii

<400> SEQUENCE: 22

| | | | | | |
|---|---|---|---|---|---|
| accactggga | ggcctcaaaa | tgactaaggt | gactgggaag | ccacaaggct | ccagagtagt | 60 |

```
tatgaaacac ctgcctcctg ttacctggga caacaggatg aagacttcct ctcaactgag        120
gtccaagaaa atgtcaagg tggccagggt acctgtgaga gtggataatc accttcaggc         180
aaagctgacc aagaaaactt ctcagaaacc acccaccaca aggaaactta aaaaaatcag        240
aggcccaaag ctctgtagct ggtgctccaa ggtgaatgaa gagctgaatc agaacggacc        300
agaagaggtc ccagagattc tgcagacccc tgtcattcca gcaggaacgg tgggcaggca        360
gtgacctcag agcatggcta gagacctcag aaatcttctg ggtcttgcc gctgagtact         420 ggccaacagt acagatgttg actattatac caactgcata cattcataat gaaaataaaa        480
tcaacctgat gtgaaattaa                                                     500
```

<210> SEQ ID NO 23
<211> LENGTH: 476
<212> TYPE: DNA
<213> ORGANISM: Bos taurus

<400> SEQUENCE: 23

```
ctcaaaatga ctaaggtgac tgggaagcca caaggctcca gagtagttag gaaacacctc         60
cctcctgtta cccaagacaa aaggatggag acctcctctc aattgaggtc caaaaaacat        120
gtcaaggtgg ccagggtaag tgtgagagtg aataatcacc ttcaggcaaa gatgaccaag        180
aaaacttctc agaaaccgcc caccacaagg aaccttagaa aaatcagagg ctcaaagctc        240
tgtagccagt gttccaaggt aaatgaagag ctgaatcaga acggaccagt ggaggtccca        300
gactgtggac acccctgtca ttccagcgga accggttggc agccagtgac ttcaaggcat        360
ggctagagac ctcagaaatc ttcgggggc ttgctgctga gtactagcca acagtacaga         420
cattgactat tataccaact gcatacatta agaatgaaaa taaaatcaac ctgatg            476
```

<210> SEQ ID NO 24
<211> LENGTH: 476
<212> TYPE: DNA
<213> ORGANISM: Bos taurus

<400> SEQUENCE: 24

```
ctcaaaatga ctaaggtgac tgggaagcca caaggctcca gagtagttag gaaacacctc         60
cctcctgtta cccaagacaa aaggatggag acctcctctc aattgaggtc caaaaaacat        120
gtcaaggtgg ccagggtaag tgtgagagtg aataatcacc ttcaggcaaa gatgaccaag        180
aaaacttctc agaaaccgcc caccacaagg aaccttagaa aaatcagagg ctcaaagctc        240
tgtagccagt gttccaaggt aaatgaagag ctgaatcaga acggaccagt ggaggtccca        300
gactgtggac acccctgtca ttccagcgga accggttggc agccagtgac ttcaaggcat        360
ggctagagac ctcagaaatc ttcgggggc ttgctgctga gtactagcca acagtacaga         420
cattgactat tataccaact gcatacatta agaatgaaaa taaaatcaac ctgatg            476
```

<210> SEQ ID NO 25
<211> LENGTH: 27
<212> TYPE: DNA
<213> ORGANISM: Artificial Sequence
<220> FEATURE:
<223> OTHER INFORMATION: forward primer for GX1 cDNA

<400> SEQUENCE: 25

```
ggtggtcata tgactaagcg gactggg                                              27
```

<210> SEQ ID NO 26
<211> LENGTH: 57

```
<212> TYPE: DNA
<213> ORGANISM: Artificial sequence
<220> FEATURE:
<223> OTHER INFORMATION: reverse primer for GX1 cDNA

<400> SEQUENCE: 26
ggtggtaact agtgcatctc ccgtgatgca accctggctg cccaccggtc ccgctgg        57

<210> SEQ ID NO 27
<211> LENGTH: 33
<212> TYPE: DNA
<213> ORGANISM: Artificial sequence
<220> FEATURE:
<223> OTHER INFORMATION: reverse primer for GX1 cDNA for in vitro
      translation

<400> SEQUENCE: 27
gtggtggtgc tcgagctggc tgcccaccgg tcc        33
```

ANTIBODY FOR SKEWING SEX RATIO AND METHODS OF USE THEREOF

This utility patent application is a Continuation of U.S. patent application Ser. No. 14/626,401 filed on Feb. 19, 2015, which claims the benefit of U.S. Patent Applications Ser. No. 62/065,797 filed on Oct. 20, 2014 and Ser. No. 61/942,020 filed on Feb. 19, 2014, the disclosures of all of which are incorporated herein by reference in their entirety.

REFERENCE TO SEQUENCE LISTING SUBMITTED ELECTRONICALLY

A sequence listing electronically submitted with the present application as an ASCII text file named 1101-013_ST25.txt, created on Feb. 12, 2015 and having a size of 20000 bytes, is incorporated herein by reference in its entirety.

TECHNICAL FIELD

The present disclosure relates to skewing sex ratios in mammals to select for a preferred gender of offspring. In particular, the disclosure relates to methods for selecting and/or altering a particular population of mammalian sperm for subsequently skewing mammalian sex ratio. The methods include providing antibodies specific for a sperm cell marker indicative of the presence of an X-chromosome, for use in such skewing and selecting.

BACKGROUND OF THE INVENTION

The XY sex-determination system is the sex-determination system found in most mammals. In this system, the sex of a mammal is determined by a pair of sex chromosomes (gonosomes) which code for the sex of the mammal. Females, being the homogametic sex, exhibit two X chromosomes. Males, being the heterogametic sex, exhibit an X and a Y chromosome. In animal husbandry it is often desirable to skew sex ratios towards either male or female offspring depending on the producer's goal. For example, in dairy cattle husbandry it is the female of the species that produces the income source for the farmer, i.e. milk. A dairy farmer utilizing artificial insemination to obtain replacement animals for the dairy herd may prefer to utilize sperm that will be biased towards production of female offspring, to ensure a reliable source of replacement heifers and so a continued income stream. Of course, similar commercial reasons exist for biasing a herd towards production of males. For example, in a beef cattle operation it is the male that provides the primary income stream (meat). Thus, improved methods of influencing sex ratio by influencing sperm sex ratio are desirable.

There are a number of potential non-invasive ways to influence sex ratio. The potential for non-invasive sex ratio manipulation is far less obvious in species in which sex chromosomes mainly determine the gender of an offspring, like in all birds and mammals. Preselecting the gender of offspring in both humans and animals has been of keen interest since the beginning of recorded history. Flow cytometric analysis of sperm DNA has been shown to very useful for evaluating the proportions of X- and Y-bearing sperm in a sample of semen. At one point, flow cytometric sorting of X- and Y-bearing sperm was shown to be the only laboratory method that skews the sex ratio of semen (Johnson, 1992).

One of the first serious scientific studies to be conducted to control prenatal sex was reported by J. L. Lush (1925). The basis for Dr. Lush's research was the possible differential density of X- and Y- bearing sperm in the rabbit. The progeny from the inseminations made with sperm separated by centrifugation failed to show altered sex ratios. Since then, innumerable reports have appeared describing a wide variety of methods to separate X- and Y-bearing sperm. The majority of these methods can be grouped under the broad heading "physical separation" methods. They are based on actual or perceived differences in the weight, density, size, motility, or surface charge of sperm. (Johnson, 1992).

Other research on the flow cytometry of sperm for the purpose of predetermining gender of offspring has led to a validated method to separate X from Y chromosome-bearing sperm for use with in vitro fertilization and embryo transfer, intratubal insemination or intracytoplasmic sperm injection (Johnson, 1995). Presently, the only commercially viable method of sexing mammalian sperm is to use a flow cytometer to measure sperm DNA content via fluorescence of the DNA-bound fluorophore Hoechst 33342, followed by sorting sperm into three populations: 1) probably X, 2) probably Y, and 3) undetermined. Millions of insemination doses of sexed sperm are produced annually by this procedure. Although accuracy of sexing usually exceeds 90%, this procedure of sexing one sperm at a time has serious limitations, including cost, sort rates, and physical damage to sperm resulting in lowered fertility, but not abnormalities in offspring.

Suggested areas for research include determining how sperm are damaged and where in the process of fertilization and embryonic development the infertility is manifest. Pre and post sorting procedures are done in approximately hourly batches, and these might be changed to continuous procedures. Numerous genetic, physical, and immunological procedures for sexing millions of sperm in parallel have been proposed, but none appears to be suitable for commercialization at this time due to issues of accuracy, repeatability, damage to sperm, and other problems. However, increasing numbers of reports are appearing concerning improvements in these procedures, and it appears inevitable that one or more of them eventually will prove to be efficacious. In developing such procedures, it is critical to monitor sexing accuracy regularly, preferably by use of rapid and inexpensive procedures which can be implemented in the commercial laboratory setting.

Recent evidence has shown that sex ratios in mammals can be manipulated by nutritional, genetic, physiological, and immunological factors. While there are several known methods for sexing sperm, each suffers from low accuracy, damage to sperm causing infertility, poor repeatability, lack of suitable scale-up procedures, or other problems. Moreover, fertility in cattle and possibly other species is compromised on the order of 10 percentage points by an unknown mechanism that appears noncompensable by increasing the number of sperm per inseminate. (Seidel, 2012). Thus, a need in the art for improved methods for sexing mammalian sperm is identified.

SUMMARY

In accordance with the foregoing need identified in the art, methods are provided for identifying mammalian X-chromosome bearing sperm cells, and for separating such sperm cells from mixed populations of sperm cells including Y-chromosome bearing sperm cells to provide an enriched X-chromosome bearing and/or an enriched Y-chromosome bearing sperm cell population. The methods are advantageously effective, repeatable, robust, and suitable for scaling up for adaptation to commercial enterprises.

In one aspect of the disclosure, an antibody, or an antigenic fragment thereof, is described which binds selectively to a mammalian sperm cell protein specific to an X-chromosome bearing sperm cell. The antibody or antigen-binding fragment thereof may be a monoclonal or a polyclonal antibody or an antigen-binding fragment thereof. In an embodiment, the mammalian sperm cell protein comprises the sequence set forth in SEQ ID NO:4. The protein may be encoded by a gene mapping to the mammalian X-chromosome and comprising the nucleotide sequence of SEQ ID NO:5 or a sequence complementary thereto, or a nucleotide sequence having at least 85% homology to SEQ ID NO: 5 or a sequence complementary thereto. The mammalian sperm cell protein (subsequently referred to herein as GX1) may comprise the sequence set forth in NCBI Accession No. XP_001249544.1.

The antibody or antigen-binding fragment thereof may be derived by immunization of a host by an antigenic peptide composition comprising a natural or a synthetic antigenic amino acid sequence set forth as SEQ ID NO: 4 or an antigenic sequence having at least 85% homology thereto. In embodiments, the antibody or antigen-binding fragment thereof is derived by immunization of the host by an antigenic peptide composition comprising peptides selected from the group consisting of one or more of SEQ ID NO: 1, SEQ ID NO: 2, and SEQ ID NO: 3.

In another aspect, the present disclosure describes methods for identifying X-chromosome bearing sperm cells in a mixed population of sperm cells. In embodiments, the method comprises adding an antibody or antigen-binding fragment thereof as described above to neat or diluted semen. Then, the labeled antibody or antigen-binding fragment thereof is directly or indirectly detected.

In yet another aspect, the present disclosure provides methods for skewing a sex ratio in mammals towards a predominantly male offspring population or a predominantly female offspring population. In embodiments, the methods comprise adding an antibody or antigen-binding fragment thereof as described above to a neat or diluted sample of mammalian semen, under conditions whereby the antibody binds to the X-chromosome bearing sperm cells. Next, oocytes are fertilized in vivo or in vitro using the semen or sperm cells isolated therefrom, at least a portion of which include bound antibody or antigen-binding fragments thereof, to skew the sex of the resulting offspring population.

In alternative embodiments, the methods further comprise separating unbound sperm cells from antibody or antigen-binding fragment-bound sperm cells to provide a sperm cell population enriched for X-chromosome bearing sperm cells and a sperm cell population enriched for Y-chromosome bearing sperm cells. Any suitable method for sorting is contemplated, including without limitation fluorescent-activated cell sorting, magnetic cell sorting, and the like. Next, oocytes are fertilized in vivo or in vitro using the population enriched for X-chromosome bearing sperm cells or the sperm cell population enriched for Y-chromosome bearing sperm cells, to skew the sex of the resulting offspring population.

The present disclosure thus responds to a need in the art by providing effective methods for identification of X-chromosome bearing sperm cells, for separation of X-chromosome and Y-chromosome bearing sperm cells, and for skewing a sex ratio of offspring resulting from fertilization with sperm cells treated as described above. Advantageously, the methods are substantially non-invasive, are reproducible, and provide a viable X-chromosome skewed sperm cell population suitable for subsequent commercial artificial insemination procedures.

BRIEF DESCRIPTION OF THE DRAWINGS

The accompanying drawing figures incorporated herein and forming a part of the specification, illustrate several aspects of the disclosure, and together with the description serve to explain certain principles thereof. In the drawings:

FIG. 2A shows presence of antibodies according to the present disclosure to a peptide having SEQ ID NO: 1 in the rabbit serum obtained 8 weeks post-immunization compared to the pre-immune rabbit serum;

FIG. 2C shows presence of antibodies according to the present disclosure to a peptide having SEQ ID NO: 3 in the rabbit serum obtained 8 weeks post-immunization compared to the pre-immune rabbit serum;

FIG. 4A depicts fluorescent photomicroscopy (Scale bar=25 microns) of sperm cells determined to be negative for association with the antibody to GX-1 of FIG. 3B;

FIG. 4B depicts fluorescent photomicroscopy (Scale bar=25 microns) of sperm cells determined to be positive for association with the antibody to GX-1 of FIG. 3B;

FIG. 7 shows a computer matching analysis of peptides derived from digestion of E. coli-expressed GX1 protein and SEQ ID NO. 4;

FIG. 11 shows a computer matching analysis of peptides derived from digestion of in vitro translation expressed GX1 protein (GX1-M) and SEQ ID NO. 4.

Figure 1A:
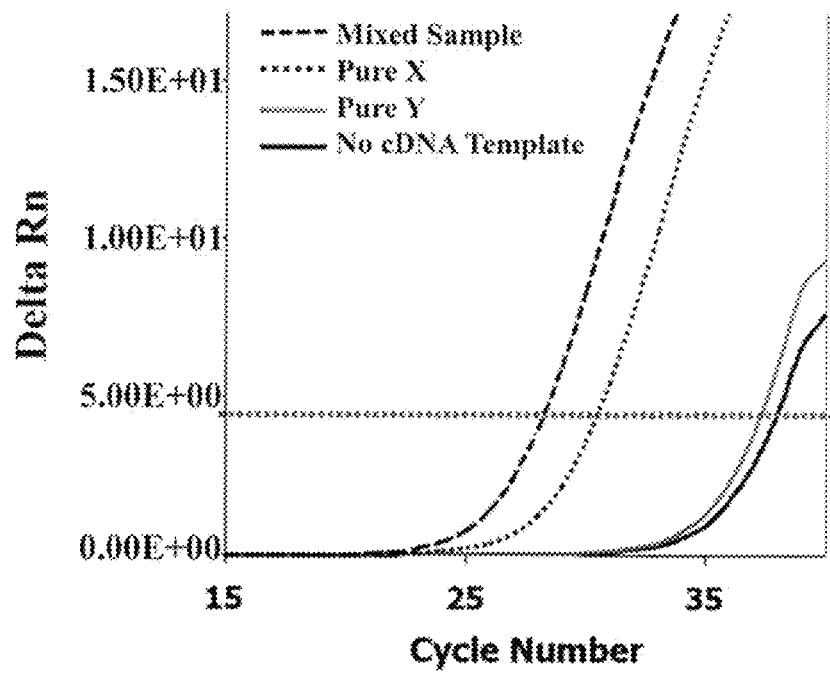
FIG. 1A shows quantitative PCR analysis of GX1 cDNA from a mixed-chromosome containing sperm cell population, a pure Y-chromosome containing sperm cell population, and a pure X-chromosome containing sperm cell population.

Reference will now be made in detail to embodiments of the disclosed subject matter, examples of which are illustrated in the accompanying drawing figures.

DETAILED DESCRIPTION

Any citations, gene sequences, accession numbers, and reference sequences included or referred to in this application form a part of the disclosure and are incorporated herein in their entirety by reference. It will be appreciated that the embodiments shown and described in this patent application are an illustration of one of the modes best suited to carry out the invention. The invention is capable of other different embodiments, and its several details are capable of modification in various, obvious aspects all without departing from the invention. Accordingly, the drawings and descriptions provided herein will be regarded as illustrative in nature and not as restrictive. Various embodiments of the methods and compositions of the present disclosure will now be described by way of the following Examples.

EXAMPLE 1

Identification of a Novel Biomarker for X-Bearing Sperm

Laser capture microdissection (LCM) was used to isolate Y-bearing sperm from nonsorted bull semen in order to identify sperm biomarkers. In brief, Percoll® prepared frozen-thawed semen from multiple Bos taurus and Bos indicus breeds was immobilized, decondensed and adhered to glass microscope slides. Sperm slides underwent in situ hybridization using the Star*FISH© paint system for the bovine Y-chromosome (Cambio Ltd; Cambridge, UK) according to the manufacturer's instructions. Fluorescence label (Cy3) on chromosome probe enabled visual classification of sex chromosome content of sperm. Using a LCM equipped microscope, single sperm cells with the desired chromosome content were lifted off the slide and "captured" onto a membrane. Total RNA isolated from each population of captured sperm cells (pure Y-chromosome containing and mixed-chromosome containing) was then compared by microarray analyses to identify a novel biomarker specific to X-chromosome bearing sperm.

After comparing the binding of 6 sets of total RNA samples (six Y-chromosome content samples versus six mixed-chromosome content samples) to GeneChip® Bovine Genome arrays (Affymetrix; Santa Clara, Calif.), it was determined that expression of an uncharacterized protein LOC781191 (SEQ ID NO: 5) was only found in RNA derived from captured sperm of mixed chromosome content and not in RNA derived from captured sperm of pure Y-chromosome content. Additionally, gene mapping by the National Center for Biotechnology Information (NCBI) located DNA for GX1 to the bovine X chromosome (NCBI, U.S. National Library of Medicine, 8600 Rockville Pike, Bethesda, Md. 20894; Gene ID 781191).

To validate microarray findings (i.e., whether the expression of the GX1 biomarker was specific to X-chromosome bearing sperm) additional sperm cells were captured from freshly prepared slides probed with the Star*FISH© paint system for either the bovine Y-chromosome or the X-chromosome (Cambio) and total RNA was isolated from the three populations of captured sperm cells: (1) Mixed-chromosome containing, (2) pure Y-chromosome containing and (3) pure X-chromosome containing. Total RNA was converted to cDNA and then subjected to quantitative polymerase chain reaction (qPCR) using primers specific to GX1 (Table 1).

Figure 1B:
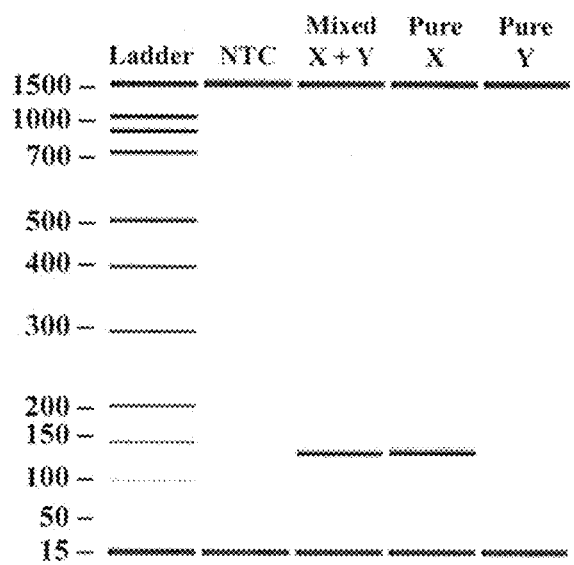
FIG. 1B shows capillary gel analysis of the cDNA of FIG. 1A.

After normalization with exogenous control, quantitative polymerase chain reaction results (FIG. 1A) indicate that detected expression of GX1 was equal between mixed chromosome containing and pure X chromosome containing samples, whereas detected expression of GX1 was equal between pure Y chromosome containing sample and no cDNA template control (NTC). Thus, based on qPCR analyses expression of GX1 was found only in cDNA derived from sperm population with X-chromosomes (i.e., pure X-chromosome containing or mixed-chromosome containing) and not in cDNA derived from pure Y-chromosome bearing sperm (see FIG. 1A). Note where sample crosses threshold (dotted line; FIG. 1A) determines threshold cycle for sample and for comparisons the lower cycle number equals greater expression level. Capillary gel analyses was utilized to confirm PCR results (FIG. 1B), with amplified DNA for GX1 only detected in the mixed chromosome containing and pure X chromosome containing samples.

TABLE 1

Sequence of primers used for quantitative polymerase chain reactions.

| Gene ID | Primer Location (bp) | Primer Sets | Anneal Temp. | Primer Conc. (nM) |
|---|---|---|---|---|
| 781191 | 4-27 | 5'-AAGCATGAGG GTGTGTCTCCCTGG (SEQ ID NO: 6) | 56° C. | 200 |
|  | 110-132 | 3'-TCCTAACTAC TCTGGAGCCTTGG (SEQ ID NO: 7) |  |  |

EXAMPLE 2

Production of Anti-GX1 Peptide Antibody

Next, polyclonal antiserum was generated in rabbits against multiple peptide antigens for GX1 protein by Bio-Synthesis Inc (Lewisville, Tex.). Specifically, the amino acid sequence for GX1 protein was derived from the DNA sequence for GX1 (SEQ ID NO:4) and analyzed for antigenic sites. Three immunograde peptides derived from 3 different antigenic sites within GX1 protein (Table 2) were synthesized utilizing FMOC chemistry under continuous flow conditions using PEG-polystyrene resins. At the completion of synthesis, peptides were cleaved from the resin, de-protected, and then precipitated using cold diethyl ether. The precipitate was then washed three times with cold diethyl ether and dissolved prior to lyophilization.

Purity and mass of peptides were evaluated by analytical-scale reverse-phase high performance liquid chromatography (HPLC) chromatogram and matrix-assisted laser desorption ionization (MALDI), respectively. For analytical and preparative HPLC, analyses and purifications were performed using a Beckman System Gold Liquid Chromatography system, equipped with a binary pump delivery system, autosampler, column thermostat, and mono-(UV), or multi-wavelength detector (DAD). Chromatography methods used were using standard conditions using 5 µm, 150×4.6 mm or 2.1 mm columns (Phenomenx or Agilent), at 20° C., with detection at λ=210, 220 or 280 nm. Mobile phase A was 0.1% TFA in ultrapure water, while mobile phase B was neat acetonitrile. The separation was obtained at a flow rate of 1.0 or 0.2 mL/min using a linear gradient program.

MALDI-TOF mass spectrometry was performed using a Voyager-DE STR Biospectrometry workstation with delayed extraction and linear capability, equipped with a 337-nm nitrogen laser and a 2-m flight tube. Mass spectra were obtained in the positive ion mode using an accelerating voltage of 25 kV. Approximately one microliter of the peptide or protein sample was mixed with 1 µl of matrix (10 mg of sinapinic acid and 0.1% 4-hydroxy-α-cyanocinnamic acid in 1 ml of distilled water) and 0.3 µl of this mixture was applied to the sample plate.

Once quality was assured, each synthesized peptide was individually conjugated to keyhole limpet hemocyanin (KLH) carrier protein and combined into a cocktail mixture. The peptide cocktail was emulsified in Freund's Complete Adjuvant and injected into a New Zealand white rabbit every two weeks for a total of five co-immunizations to induce GX1 antiserum production. Serum was collected prior to primary immunization (pre-immune; week 0), fourth booster injection (week 8), two weeks after the fourth booster injection (week 10) and upon termination of project (week 14). Seras collected at weeks 0 and 8 were analyzed by enzyme-linked immunosorbent assay (ELISA) titer assay for each antigen peptide to ensure specificity of antiserum.

For the ELISA titer assay, briefly, microtiter plate wells were first coated at room temperature with peptide solution in coating buffer (PBS) and were then blocked with 1% BSA in PBS for 1 h at 37° C. Samples, antibodies in serum or purified, were loaded in duplicates and incubated for 2 h at room temperature. Secondary HRP-conjugated IgGs (1:20,000) in blocking buffer was added (1 h, room temperature) and the reaction was visualized by the addition of the chromogenic substrate (ABTS) for 30 min. The absorbance at 405 nm was measured using an ELISA plate reader. Plates were washed four times with washing buffer [PBS, pH 7.4, containing 0.1% (v/v) TWEEN 20; polyoxyethylene (20) sorbitan monolaurate] after each step. As a reference for quantification, a standard curve was established by a serial dilution of control antibody.

Figure 2B:
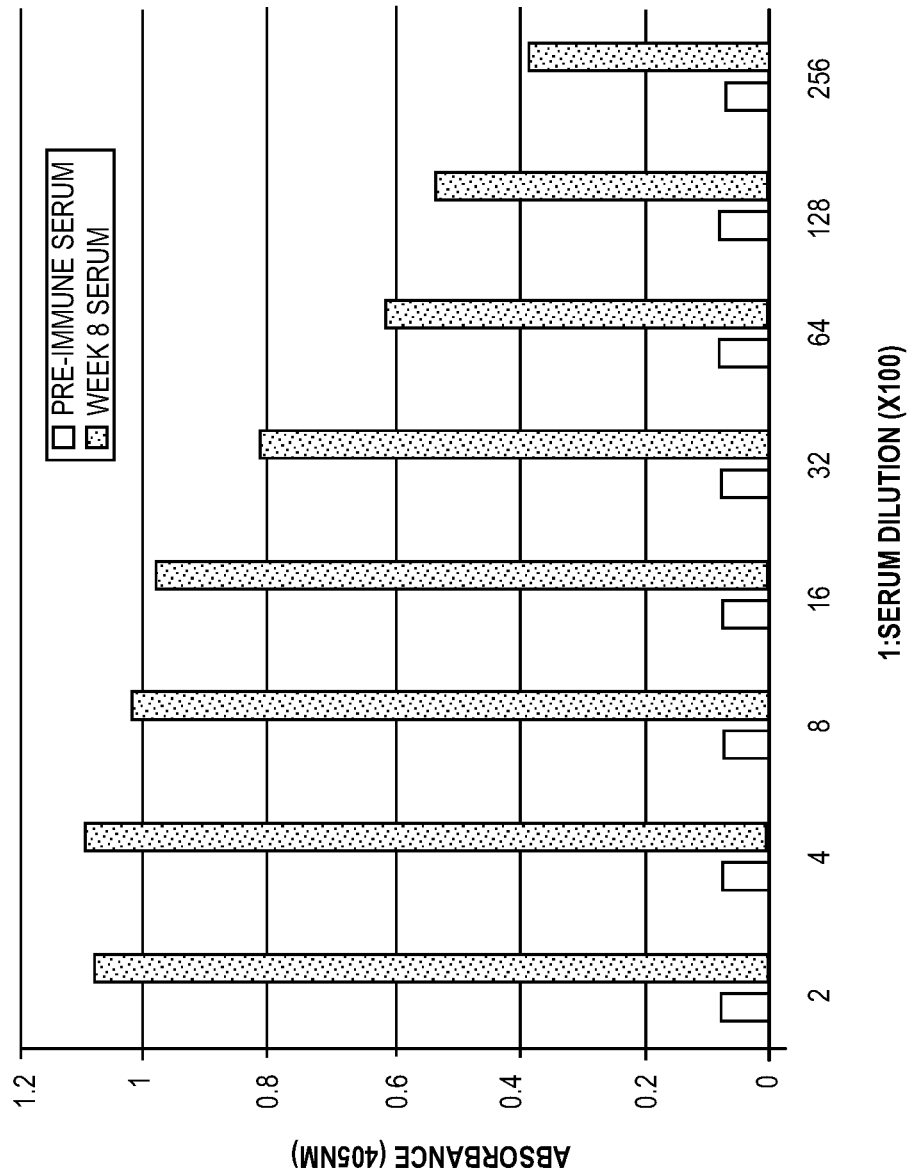
FIG. 2B shows presence of antibodies according to the present disclosure to a peptide having SEQ ID NO: 2 in the rabbit serum obtained 8 weeks post-immunization compared to the pre-immune rabbit serum.

Results from ELISA indicated that pre-immune serum lack antibodies reactive to the three peptide antigens (i.e., values for absorbance at 405 nm less than 0.1) for all dilutions tested. Week 8 serum contained antibodies reactive to the three peptide antigens as indicated by binding of antibody(s) to wells coated with peptide antigens (i.e., values for absorbance at 405 nm greater than 0.1) for all dilutions tested (see FIGS. 2A, B, C).

Peptide conjugated resin columns were used to purify and concentrate antibodies specific for peptide antigens from GX1 antiserum by immunoaffinity chromatography, thus generating anti-GX1 peptide antibody. Upon arrival in the laboratory, specificity of the antibodies for a single protein was determined by western blot analyses comparing reactivity of pre-immune serum, anti-GX1 peptide antibody and preabsorbed anti-GX1 peptide antibody on bull sperm lysate.

Figure 3A:
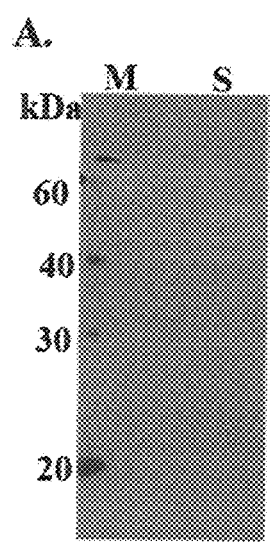
FIG. 3A shows a western blot analysis indicating specificity of an antibody to GX-1 protein according to the present disclosure in pre-immune rabbit serum.
Figure 3B:
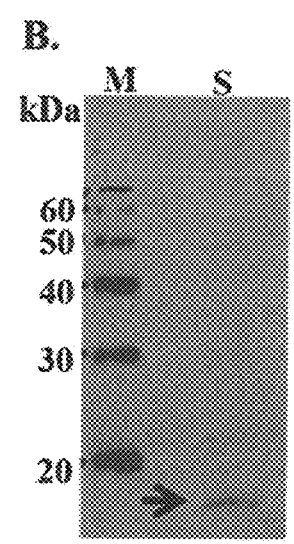
FIG. 3B shows a western blot analysis indicating specificity of an antibody to GX-1 protein according to the present disclosure in rabbit serum obtained 8 weeks post-immunization.
Figure 3C:
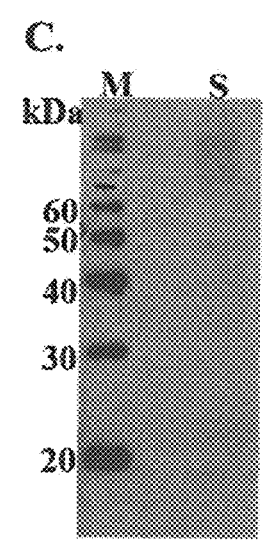
FIG. 3C is a western blot demonstrating that pre-absorbing the antibody of FIG. 3B with peptides having SEQ ID NO: 1, SEQ ID NO:2, and SEQ ID NO:3 eliminated detection of GX-1 protein.

In brief, sperm lysates were separated on SDS-12% polyacrylamide gel and transferred to PVDF membrane. The results are presented in FIG. 3. In the figure, M=protein standard, and S=sperm lysate. As shown, immunoblotting sperm lysates with preimmune serum did not detect any protein bands (FIG. 3A) whereas probing with anti-GX1 peptide antibody detected a single protein band (FIG. 3B, see arrow) in the bull sperm lysate. Preabsorbing anti-GX1 peptide antibody with peptide antigens prior to probing the western blot eliminated detection of the protein band in sperm lysate (FIG. 3C).

TABLE 2

Sequence of synthetic peptides used to immunize rabbits to produce GX1 antiserum.

| Peptide No. | Amino acid sequence (N-terminus to C-terminus) | Epitope position |
|---|---|---|
| 1 | CTKRTGKPQSSRVVRKHLPP (SEQ ID NO: 1) | 2-20 |
| 2 | CKTSSQLRPPKNVKVARASAR (SEQ ID NO: 2) | 28-47 |
| 3 | CKVNEELNQNGPEEVPESVE (SEQ ID NO: 3) | 83-102 |

EXAMPLE 3

Incubation of Anti-GX1 Peptide Antibody with Bull Semen

For the following studies, commercially available extended and cooled semen was used. In brief, ejaculate was collected from bulls (multiple Bos taurus and Bos indicus breeds were tested, specifically Angus, Cross, and Red Brangus), mixed with BIOXcell extender (IMV Technologies, Maple Grove MN) and equilibrated at 4-5° C. for 3 h prior to shipping overnight on ice packs. Upon arrival at the laboratory, semen was washed with HEPES-PVA buffer (prewarmed to 25-30° C.; 114 mM NaCl, 3.2 mM KCl, 0.3 mM $NaH_2PO_4$, 10 mM Lactic Acid, 2 mM $CaCl_2$, 0.5 mM $MgCl_2$, 10 mM HEPES. 2 mM $NaHCO_3$, 0.2 mM Na Pyruvate, 0.1% PVA). Sperm pellets were resuspended in HEPES-PVA containing 1:1000 dilution of Live/Dead® Fixable Far Red (Life Technologies, Grand Island, NY) dead cell stain and then incubated for 10 min at 35° C. Sperm were washed once with HEPES-PVA to remove excess stain and then resuspended to a final concentration of $10 \times 10^6$ cells/mL HEPES-PVA.

One milliliter of sperm suspension was transferred to round bottom Protein LoBind tubes and then centrifuged at 4° C. at ×400 g for 5 min, supernatant removed and sperm pellets gently vortexed (these conditions were used for all subsequent centrifugations). Throughout remaining steps, sperm and buffers were kept at 4° C. After centrifugation, sperm pellets were suspended in 1 mL blocking buffer [3% normal goat serum (NGS; Southern Biotech, Birmingham, Ala.) and 2 mM EDTA in Dulbecco's Phosphate Buffered Saline (DPBS; Gibco® Life Technologies)]. Sperm were incubated for 30 min with gentle agitation then subjected to centrifugation. Resulting sperm pellets were suspended in 1 mL blocking buffer containing anti-GX1 peptide antibody (0 to 20 µg/mL) and incubated for 1.5 h with gentle agitation. Then wash buffer (1 mL; 0.5% NGS, 2 mM EDTA, DPBS) was added to each tube prior to centrifugation. Sperm were subjected to a second wash before suspension in 0.5 mL wash buffer containing 1.5 µg anti-rabbit IgG-cyanine dye conjugate (Cy2; Jackson ImmunoResearch Laboratories, West Grove, Pa.).

Sperm were incubated for 20 min with gentle agitation prior to washing twice with wash buffer and fixing with 1% paraformaldehyde (15 min; freshly prepared from 16% paraformaldehyde; Electron Microscopy Sciences, Hatfield, Pa.). Fixed cells were centrifuged, washed, centrifuged and finally suspended with 0.1% PVA in DPBS. Percent of membrane intact sperm positive for GX1 protein surface staining (cells positive for Cy2 and negative for Live/Dead® Far Red) was determined using a BD Accuri C6 flow cytometer (BD Biosciences, San Jose, Calif.). Samples were stored at 4° C. and protected from light until further analyses could be performed.

EXAMPLE 4

Isolation of Bull Sperm Positive for Anti-GX1 Peptide Antibody Association

A FACSAria II Special Order System (2-laser 6 color 4B-2R; BD Biosciences) with 50 mW of 488 nm laser and 100 mW of 640 nm laser was utilized to separate bovine sperm. The system was configured with 1.0 neutral day filter plus a 70 µm nozzle tip at a sheath pressure of 70 psi using BioSure® preservative-free sheath fluid (BioSure; Grass Valley, Calif.). Detectors included forward scatter area, height, width (FSC-A; -H; -W), side scatter area, height width (SCC-A; -H; -W) for singlet discrimination, 488 nm laser (FITC-A) with a 530/30 nm filter set and a 505 nm long pass mirror to detect cells labeled with Cy2 (cells positive for GX1 protein) as described above and 640 nm laser (APC-A) with a 670/30 nm filter and a 750 nm long pass mirror to discriminate absence or presence of Live/Dead® Far Red staining. All samples were processed at 4° C. and collected into 12×75 mm BSA coated tubes in sheath fluid. A portion of each sample was analyzed on BD FACSDiva 6.1.3 prior to and post-sorting to determine percent of membrane intact sperm positive for GX1 protein.

Sorting for absence or presence of anti-GX1 peptide antibody association, i.e. sorting a mixed sperm cell population to purify for absence or presence of anti-GX1 peptide antibody association, was confirmed using fluorescent microscopy (see FIGS. 4A, 4B; scale bar=25 microns). Cells were exposed to anti-GX1 antibody and to anti-rabbit IgG-cyanine dye conjugate (Cy2) as described above to detect cells positive for association with anti-GX1 peptide antibody, and counterstained with DAPI. As shown, membrane-intact cells sorted to provide a population of sperm cells negative for association with anti-GX1 peptide antibody did not label with Cy2 (FIG. 4A), whereas membrane-intact cells sorted to provide a population of sperm cells positive for association with anti-GX1 peptide antibody labeled with Cy2 (FIG. 4A).

EXAMPLE 5

Sex Ratio of Bull Sperm Positive for Anti-GX1 Peptide Antibody Association

Each sorted sample (see Example 4 above) was spun onto a clean uncoated cytospin glass slide (Thermo Scientific Inc, Waltham, Mass.) using a cytocentrifuge (settings 1000 rpm for 5 min) with a disposable single cytofunnel (Thermo Fisher Scientific). Immediately after removal from the cytofunnel clip, each slide was subjected to a decondensation procedure modified from Rens et al. (2001). Specifically, solution A (10 mM Tris, 154 mM NaCl) was placed onto the sperm spot, then equal volume of solution B (freshly prepared 50 mM DTT in solution A) was added to the droplet. After 2.5 min at room temperature, an equal volume of modified solution C (1% SDS, 100 mM Disodium tetraborate) was added to the droplet. Slides were incubated for 10s prior to placement into prechilled 100% EtOH (−20° C.). Slides were then incubated for 15 min at −20° C. and then dried at room temperature. Subsequent rehydration, permeabilization and dehydration were performed as follows: 5 min in DPBS twice, 15 min in 200 mM HCl freshly prepared in $H_2O$, 5 min in 2 X SSC, 2 min in 70% EtOH, 2 min in 90% EtOH, 2 min in 100% EtOH and then dried at room temperature. A probe mixture for bovine Y chromosome was prepared concurrent with slide processing; 5 µM peptide nucleic acid probe [Cy3-OO-AGCCCTGTGCCCTG; SEQ ID NO: 8; sequence derived from Perret et al. (1990)] in 50% deionized formamide, 10% dextan sulfate, 2 X SSC was incubated for 10 min at 75° C. and held at 37° C. until use.

Dried slides were placed onto a prewarmed Omnislide thermal cycler (37° C.) and prepared probe was then deposited onto the sperm spot with a glass coverslip; edges were sealed with rubber cement. Slides were subjected to 2 min at 75° C. prior to incubating at 37° C. for a minimum of 18 h. Following hybridization incubation, rubber cement was carefully removed without disturbing the coverslip placement; then slides were placed into DPBS with 0.1% TWEEN 20 and agitated for 2 min to gently remove coverslips. Excess probe was washed from slides by incubating in DPBS-0.1% TWEEN 20 at 45° C. for 15 min then in 2 X SSC-0.05% TWEEN 20 for 5 min. Glass coverslips were mounted over the sperm spot on each slide using Prolong Gold® mounting media with DAPI (Life Technologies). For quality control, the assay included slides prepared from nonsorted sperm as well as X- or Y-sorted sperm (Select Sires Inc, Plain City, Ohio). Two observers uninformed of treatments evaluated sperm for presence or absence of Y chromosome (presence or absence of Cy3 punctate spot within the sperm head) to determine percent of Y- and X-bearing sperm in each sample.

Figure 5:
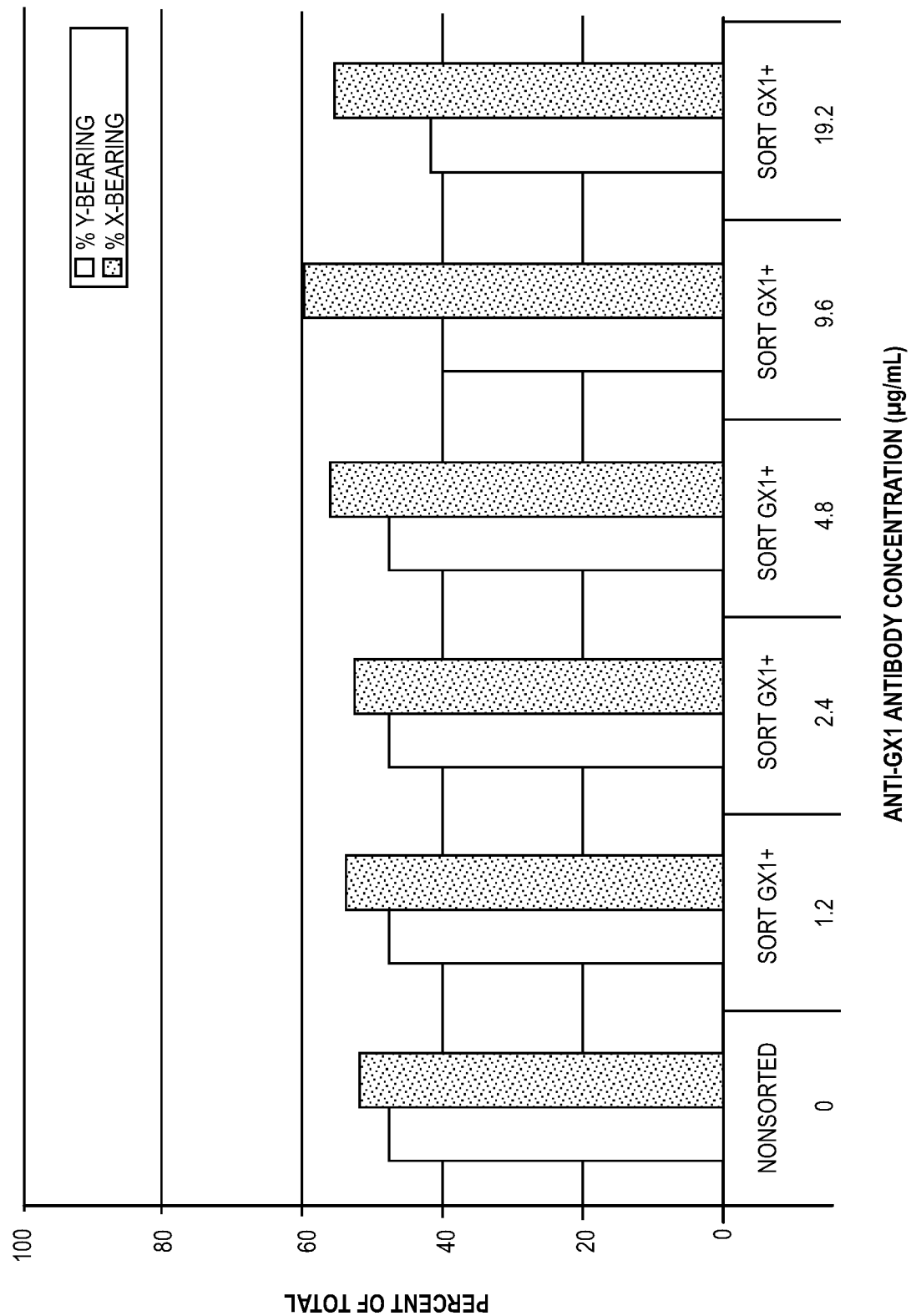
FIG. 5 graphically illustrates a sex ratio of bovine sperm cells that is skewed towards X-chromosome bearing sperm cells following incubation with the antibody to GX-1 of FIG. 3B and selection of intact sperm positive for association with the antibody of FIG. 4B.

Selecting for membrane intact sperm that were positive for anti-GX1 peptide antibody association resulted in skewing towards X-bearing sperm with certain concentrations of the anti-GX1 peptide antibody. As the concentration of anti-GX1 peptide antibody incubated with the bull sperm was increased, the proportion of X-chromosome bearing sperm being increased within the population selected to be positive for association with anti-GX1 peptide antibody. In other words, increasing the concentration of anti-GX1 peptide antibody incubated with the bull sperm resulted in the proportion of X-bearing sperm being increased within the population selected to be positive for association with anti-GX1 peptide antibody (FIG. 5).

EXAMPLE 6

Association of Anti-GX1 Peptide Antibody with Bull, Stallion, Man, Ram, Boar and Buck Sperm The ability of anti-GX1 peptide antibody to bind to sperm of various species was evaluated on semen freshly collected from bull and stallion as well as extended/frozen semen from man, ram, boar and buck (Cervidae). First, semen collected from these species was washed twice with DPBS to remove extender and/or seminal fluid. Semen pellets were resuspended in DPBS and spotted onto uncoated glass microscope slides. Slides were allowed to dry for 10 min at room temperature before fixation in −20° C. Methanol (100% ACS grade; Thermo Fisher Scientific Inc.). Slides were incubated for 10 min at −20° C. then allowed to dry completely in a fume hood for a minimum of 10 min.

The area around the sperm spot location was encircled using hydrophobic ink (GnomePen; FroggaBio Inc, Toronto, ON Canada). Sperm cells were rehydrated in DPBS containing 1:500 dilution of Live/Dead® Fixable Violet (Life Technologies) cell stain and then incubated for 30 min at room temperature in a humidified chamber with protection from light (conditions used for all subsequent incubations unless otherwise noted). Rehydration liquid was wicked off the slides and replaced with 10% NGS in DPBS to block nonspecific binding sites. Slides were incubated for 1 h at room temperature.

After wicking the blocking solution from the slides, 3% NGS-DPBS containing 0.5 or 5 µg/mL anti-GX1 peptide antibody (aka primary antibody) was placed on slides after absorption without or with the 3 peptide antigens (ratio 1 antibody to 10 of each peptide antigen; see Table 2). Slides containing a mix of primary antibody and peptide antigens function as absorption control [nomenclature based on Burry, R. W. (2011)]. For additional controls, two slides were covered with 3% NGS-DPBS; i.e., no primary antibody. All slides were incubated overnight at 4° C.

After wicking liquid from the slides, the sperm spots were washed three times with DPBS at room temperature, incubating for 5 min per wash. Then 3% NGS-DPBS containing 1:1000 dilution of anti-rabbit IgG-Cy3 conjugate (secondary antibody; Jackson ImmunoResearch Laboratories) was placed onto each sperm spot. The slides were then incubated for 15 min at room temperature. Of the control slides, the one incubated with secondary antibody serves as secondary control to discern nonspecific binding of the Cy3 conjugate. The remaining control slide was incubated with 3% NGS-DPBS omitting the secondary antibody; this is the labeling control to determine endogenous fluorescence.

After wicking liquid from slides, the sperm spots were washed three times with DPBS at room temperature, incubating for 5 min per wash. Glass coverslips were mounted over the sperm spot on each slide using Prolong Gold® mounting media with DAPI (Life Technologies). Slides were evaluated using an Arcturus® LCM system equipped with Nikon Eclipse Ti-E inverted research microscope, 40 & 60× objectives, and epi-fluorescence (Life Technologies). Fixed stained sperm were evaluated for the presence of GX1 protein by visualizing the attachment of anti-rabbit IgG-Cy3 conjugate to sperm presumably through specific binding of the anti-GX1 peptide antibody. A fluorescent filter with excitation for 510-560 nm and emission for >590 nm was utilized to evaluate the specific staining with anti-GX1 peptide antibody. The counterstains were used to localize where the binding occurred on sperm; Live/Dead® Fixable Violet and DAPI were visualized using a fluorescent filter with excitation for 325-375 nm and emission for >420 nm.

Of the sperm the anti-GX1 antibody associated with, it was localized to the upper head region in the bovine. In human sperm, anti-GX1 antibody was associated with the tail. Of the horse, sheep and deer sperm in which anti-GX1 was associated, localization was noted in the tail with several sperm also having some localization in the lower head region. In boar sperm, association of anti-GX1 was observed in the lower head region of some sperm. Control slides were evaluated with same exposure settings that were used to examine the anti-GX1 peptide antibody labeled samples. For all species (bovine, human, equine, ovine, cervidae and porcine) tested, association with anti-GX1 peptide antibody was absent on sperm on all control slides: absorption, secondary and labeling. The anti-GX1 antibody did not bind to every sperm cell, further supporting specificity to X-chromosome bearing sperm cells.

EXAMPLE 7

Synthesis and Purification of GX1 Protein using *E. coli*

A clone of GX1 mRNA was generated by PCR amplification of cDNA derived from bovine testes RNA. An amplicon sized approximately 439 bp was ligated into the TA cloning vector (pGEM-T Easy, Promega, Madison, Wisc.). Once identity was confirmed by sequencing, the plasmid containing the GX1 cDNA was subjected to PCR to generate a cDNA fragment which consists of nucleotide sequence for the protein coding region for GX1 flanked by restriction enzyme cleavage sites for subsequent ligation into *E. coli* protein expression vector. Specifically, the forward primer was designed to add an Nde I cleavage site immediately prior to start codon of the GX1 coding region whereas the reverse primer was designed to replace the stop codon of the GX1 coding region with sequences for a glycine amino acid, an intein-chitin binding domain tag and a Spe I cleavage site (Table 3). The products of the PCR were subjected to digestion with appropriate restriction enzymes prior to ligation into digested pTXB1 vector [New England Biolabs Inc (NEB), Ipswich, MA] and transformation into *E. coli* JM109 cells (NEB). Plasmids were isolated from transformants and then screened for presence of GX1 cDNA insertion by restriction digestion. Positive clones were sequenced to insure that GX1 cDNA was in the proper orientation to the intein tag for C-terminus labeling then transformed into *E. coli* T7 Express cells (contains T7 RNA polymerase gene; NEB).

TABLE 3

| Sequence of primers used to generate GX1 cDNA insert for expression using *E. coli* ||
| --- | --- |
| Primer | Sequence* |
| Forward | 5'-GGT GGT <u>CAT ATG</u> ACT AAG CGG ACT GGG-3' (SEQ ID NO: 25) |
| Reverse | 5'-GGT GGT <u>AAC TAG</u> TGC ATC TCC CGT GAT GCA ACC CTG GCT GCC CAC CGG TCC CGC TGG-3' (SEQ ID NO: 26) |

*Restriction enzyme cleavage sequence underlined

To express intein tagged GX1 protein, LB media was inoculated with a T7 Express cell transformant, cells cultured to density of 0.4 to 0.6 $OD_{600}$ and then induced with addition of isopropyl-beta-D-thiogalactoside (IPTG). After 2-4 h of incubation, cells from IPTG-induced culture were collected, lysed, and loaded onto a chitin resin column. The GX1 fusion protein was immobilized onto the chitin resin through binding of the intein-chitin binding domain tag. The column was washed to remove nonspecific binding of non-GX1 fusion proteins. The GX1 protein was released from the column through induction of the intein cleavage by the addition of dithiothreitol-containing buffer.

Figure 6:
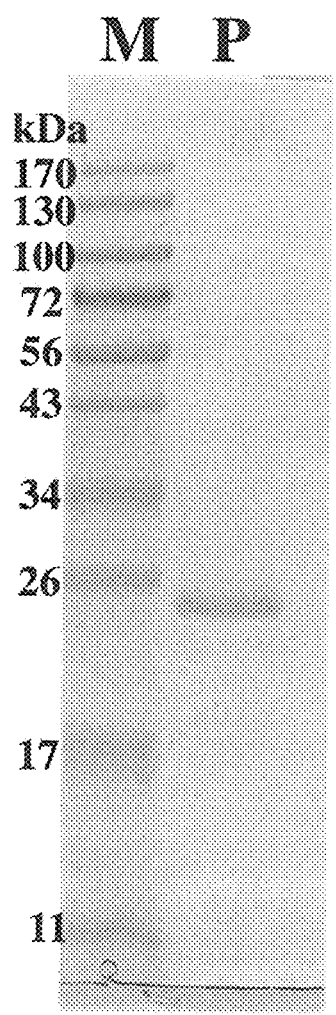
FIG. 6 depicts an evaluation of purity of E. coli expressed GX1 full length protein via SDS-12% polyacrylamide gel counterstained to visualize protein banding pattern.
Figure 8:
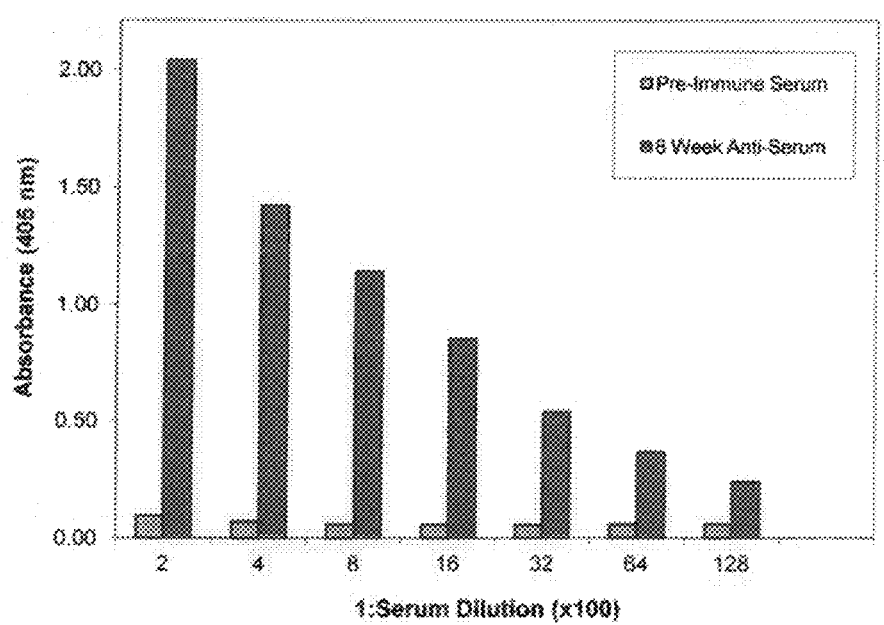
FIG. 8 graphically depicts the presence of antibodies in week 8 antiserum compared to pre-immune serum from rabbit immunized with full length GX1 protein expressed and purified from E. coli cells, (GX1-E protein)
Figure 9:
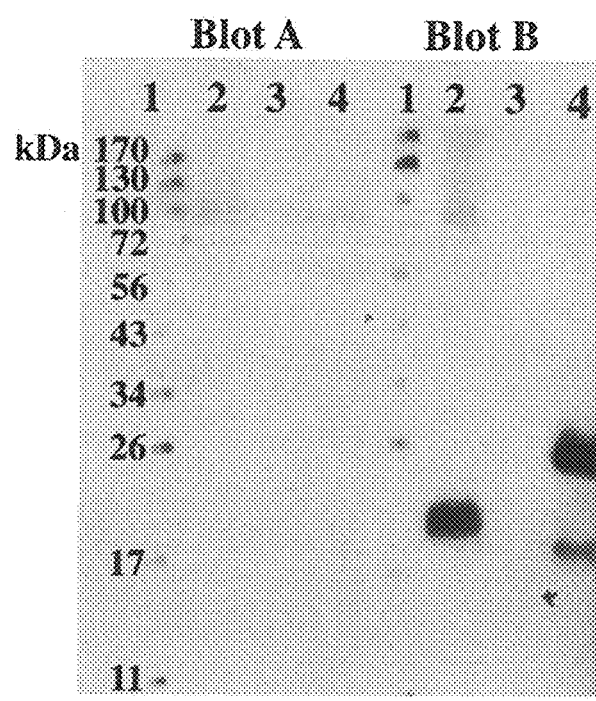
FIG. 9 illustrates specificity of anti-GX1-E protein antibody for a single protein in bull sperm lysate by western blot analyses of pre-immune serum (Blot A) and purified anti-GX1-E protein antibody (Blot B) on bull sperm lysate.
Figure 10:
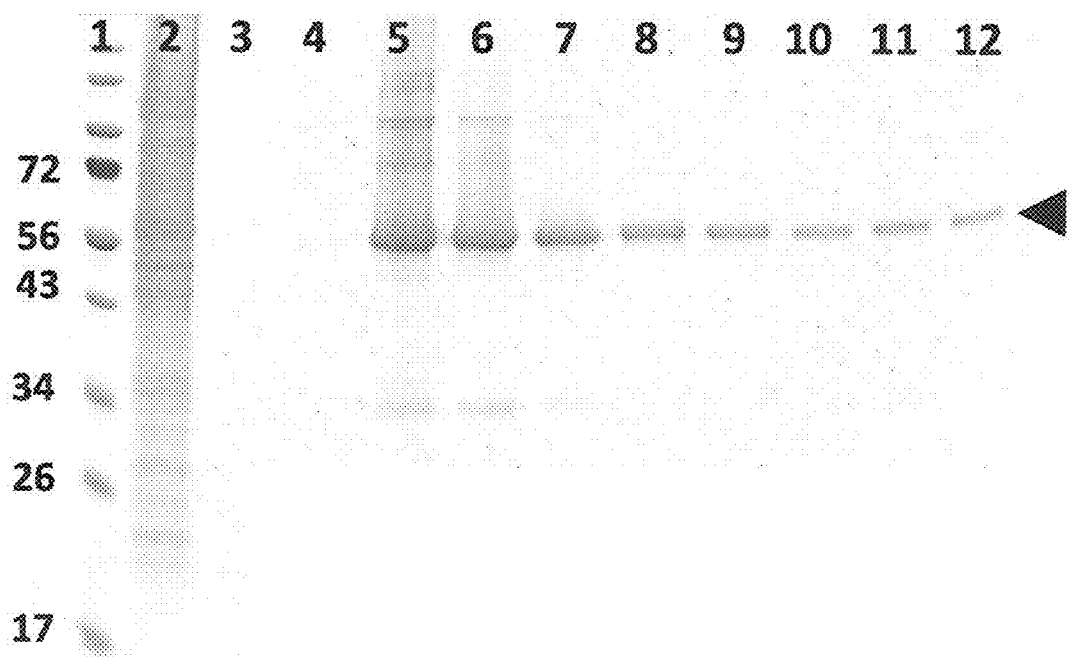
FIG. 10 shows evaluation of GX1 full length protein expressed using in vitro translation (GX1-M; the arrow indicates the location of the GX1-M protein)

Following elution, the *E. coli* expressed GX1 protein (hereafter abbreviated as GX1-E) was dialyzed with PBS, concentrated using an Amicon® ultra centrifugal device (10K MWCO; EMD Millipore, Billerica, Mass.) and purity confirmed by SDS-PAGE (see FIG. 6; M=protein standard; P=dialyzed and concentrated protein). Only a single band of protein was visible on the stained gel. The GX1-E protein was sent to a commercial company for confirmation of protein identity. Upon arrival at the company, the GX1-E protein was digested with trypsin and the resulting peptides were analyzed by LC/MS/MS (MS Bioworks LLC, Ann Arbor, Mich.). Computer analysis matched the peptide sequences to the GX1 protein sequence with 86% coverage (see FIG. 7; 98/114 amino acids matched, light grey areas indicate location of peptide matching and dark grey areas indicate identification of modified amino acid).

EXAMPLE 8

Production of Anti-GX1 Protein Antibody from *E. coli* Expressed GX1 Protein

Polyclonal antiserum was generated in rabbits against GX1-E protein prepared as described in Example 7. Briefly, the GX1-E protein was emulsified in Freund's Complete Adjuvant and injected into a New Zealand white rabbit every two weeks for a total of seven co-immunizations to induce GX1-E antiserum production. Serum was collected prior to primary immunization (pre-immune; week 0), prior to fourth booster injection (week 8), two weeks after the fourth booster injection (week 10), prior to seventh booster injection (week 14), one week after the seventh booster injection (week 15) and upon termination of project (week 17).

Sera collected at weeks 0 and 8 were analyzed by ELISA titer assay to ensure specificity of antiserum for GX1-E protein. Results from ELISA indicated that pre-immune serum lack antibodies reactive to the GX1-E protein whereas the serum collected at week 8 contained high concentrations of antibodies (i.e., high titers) for the GX1-E protein. As shown in FIG. 8, pre-immune serum lacked antibodies reactive to the GX1-E protein (values for absorbance at 405 nm less than 0.1) for all dilutions tested whereas week 8 serum contained antibodies reactive to the GX1-E protein (values for absorbance at 405 nm greater than 0.1) for all dilutions tested.

Protein conjugated resin columns were used to purify and concentrate antibodies from week 10 antiserum (immunoaffinity chromatography), thus generating purified anti-GX1-E protein antibody (deposited with the American Type Culture collection (ATCC) on Apr. 2, 2019, Patent Deposit Designation PTA-125897). Upon arrival in the laboratory, specificity for a single protein was determined by western blot analyses comparing reactivity of pre-immune serum (FIG. 9, Blot A) and purified anti-GX1-E protein (FIG. 9, Blot B) on bull sperm lysate. Immunoblotting sperm lysates with pre-immune serum did not detect any protein bands whereas probing with anti-GX1-E protein antibody detected a single protein band in bull sperm lysate and the control GX1-E protein (FIG. 9; lane 1=protein standard; lane 2=bull sperm lysate; lane 3=blank; lane 4=purified GX1-E protein).

EXAMPLE 9

Synthesis and Purification of GX1 Protein using a Mammalian In Vitro Protein Expression System The clone of GX1 mRNA (Example 7) was subjected to PCR to generate a cDNA fragment which consists of nucleotide sequence for the protein coding region for GX1 flanked by restriction enzyme cleavage sites for subsequent ligation into protein expression vector. Specifically, the forward primer was designed to add an Nde I cleavage site immediately prior to start codon of the GX1 coding region whereas the reverse primer was designed place an Xho I immediately following the stop codon of the GX1 coding region (Table 4).

TABLE 4

Sequence of primers used to generate GX1 cDNA insert for in vitro translation

| Primer | Sequence* |
|---|---|
| Forward | 5'-GGT GGT CAT ATG ACT AAG CGG ACT GGG-3' (SEQ ID NO: 25) |
| Reverse | 5'-GTG GTG GTG CTC GAG CTG GCT GCC CAC CGG TCC-3' (SEQ ID NO: 27) |

*Restriction enzyme cleavage sequence underlined

The products of the PCR were subjected to digestion with appropriate restriction enzymes prior to ligation into digested pT7CFE1-NHIS-GST-CHA vector (Thermo Fisher Scientific) and transformation into *E. coli* JM109 cells (NEB). Plasmids were isolated from transformants and then screened for presence of GX1 cDNA insertion by restriction digestion. Positive clones were sequenced to insure that GX1 cDNA was in the proper orientation to the hexahistidine (His)—glutathione S-transferase (GST) tag for N-terminus labeling. Purified plasmid DNA from positive clones was used with the 1-step human high-yield in vitro translation kit (Thermo Fisher Scientific) following manufacturer instructions to synthesize His-GST tagged GX1 protein. In vitro translation reactions diluted in xTractor® buffer (Clontech Laboratories Inc, Mountain View, Calif.) were loaded onto a His TALON gravity column (Clontech). The passage of the diluted reactions across the column allows for immobilization of the His-GST GX1 fusion protein to the cobalt resin through binding of the hexahistidine tag. The column was washed to remove nonspecific binding of non-GX1 proteins. The GX1 protein was released from the column through the addition of discrete volumes of imidazole-containing buffer.

Purity of the His-GST GX1 fusion protein in each elution volume was evaluated (see FIG. 10) by SDS-PAGE (on SDS-12% polyacrylamide gel), comparing a protein standard (lane 1) to in vitro translation reaction (lane 2) prior to binding to cobalt resin column and the elution of immobilized protein with discrete volumes of imidazole-containing buffer (lanes 3 to 10). Elutions deemed to contain only the in vitro expressed GX1 protein (hereafter abbreviated as GX1-M) were combined for dialysis with PBS and then concentrated using Amicon® ultra centrifugal device (10K MWCO; EMD Millipore) prior to shipment to commercial company for confirmation of protein identity. Upon arrival at the company, the GX1-M protein was digested with trypsin and the resulting peptides were analyzed by LC/MS/MS (MS Bioworks LLC). Computer analysis matched the peptide sequences to the GX1 protein sequence with 87% coverage (FIG. 11; 99/114 amino acids; light grey areas indicate location of peptide matching and dark grey areas indicate identification of modified amino acid).

EXAMPLE 10

Identification of Variants of SEQ ID NO: 4

Variants were identified comprising amino acid sequences determined to deviate by one or more amino acid residues from the sequence set forth in SEQ ID NO: 4 with minimal influence on the antigenic properties of the resulting variant protein. Each variant protein contained one or more of the peptide regions set forth herein as SEQ ID NO: 1, 2, and 3. Variants were identified by the BLASTNP software (NCBI) as having at least 79%, 85%, 90% or 95% identity with the amino acid sequence set forth in SEQ ID NO: 4. The variants of the X-chromosome-bearing mammalian sperm cell protein comprise the amino acid sequences set forth in SEQ ID NO: 9-16, and the proteins for the variants of the X-chromosome-bearing mammalian sperm cell protein may be encoded by the nucleotide sequences set forth in SEQ ID NO: 17-24.

Computer analyses as summarized above determined that the evaluated variant protein sequences exhibited high sequence homology with the GX1 and would be specifically bound by the anti-GX1 peptide antibody (Example 2) as well as an antibody against the full length protein (Examples 8 and 11; see infra). The computer analysis showed the following homologies to the GX1 protein sequence (SEQ ID NO: 4) for certain variants: SEQ ID NO: 9 (Gene ID: 781267)=98%; SEQ ID NO: 10 (Gene ID: 100336610)=92%, SEQ ID NO: 11 (Gene ID: 781072)=91%, SEQ ID NO: 12 (Gene ID: 100299333)=90%, SEQ ID NO: 13 (Gene ID: 102327690)=81%, SEQ ID NO: 14 (Gene ID: 102328632)=79%, SEQ ID NO: 15 (Gene ID: 100337198)=85%, and SEQ ID NO: 16 (Gene ID: 100337198 isoform)=82%.

EXAMPLE 11

Production of Anti-GX1 Protein Antibody from In Vitro Expressed GX1 Protein

Polyclonal antiserum will be generated in rabbits against GX1-M protein by Bio-Synthesis Inc. Specifically, the GX1-M protein will be emulsified in Freund's Complete Adjuvant and then injected into a New Zealand white rabbit every two weeks for a total of five co-immunizations to induce GX1-M antiserum production. Serum will be collected prior to primary immunization (pre-immune; week 0), fourth booster injection (week 8), two weeks after the fourth booster injection (week 10) and upon termination of project (week 14). Sera collected at weeks 0 and 8 will be analyzed by ELISA titer assay to ensure specificity of antiserum. Protein conjugated resin columns will be used to purify and concentrate antibodies from GX1-M antiserum (immunoaffinity chromatography), thus generating purified anti-GX1-M protein antibody. Upon arrival in the laboratory, specificity for a single protein will be determined by western blot analyses comparing reactivity of pre-immune serum, anti-GX1-M protein antibody (deposited with the American Type Culture collection (ATCC) on Apr. 2, 2019, Patent Deposit Designation PTA-125898) and preabsorbed anti-GX1-M protein antibody on bull sperm lysate.

EXAMPLE 12

Skewing Sex Ratio in Offspring after Separating Sperm

Antibody or antigen-binding fragment according to Examples 2, 8 and/or 11 is labeled with a detectable substance, without intending any limitation including fluorescent, radioactive, enzymatic, or protein labels. Antibody or antigen-binding fragment may be conjugated to solid supports, such as, but not limited to, tubes, beads, and/or plates. Then the labeled and/or conjugated antibody or antigen-binding fragment is added to neat or diluted sample of mammalian semen and/or sperm under conditions whereby the antibody binds to the X-chromosome bearing sperm cells. Next, sperm cells bound to the antibody are separated from unbound sperm cells. Any suitable method for separating is contemplated, including without limitation fluorescent-activated cell sorting, magnetic cell sorting, adherence to antibody-coated tubes, adherence to antibody-coated plates, adherence to antibody-coated beads, adherence to other solid matrices, and the like. Separated sperm cells then may be used immediately to inseminate females or fertilize oocytes in vitro or are processed and frozen using conventional methods known in the art to allow for use to inseminate and/or fertilize in vitro upon a later date.

EXAMPLE 13

Skewing Sex Ratio in Offspring without Separating Sperm

An antibody or antigen-binding fragment thereof derived as described in Examples 2, 8 and/or 11 is added to neat or diluted sample of mammalian semen and/or sperm under conditions whereby the antibody/antigen-binding fragment binds to the X-chromosome bearing sperm cells and provides a physical barrier preventing the antibody-bound sperm cells from fertilizing an oocyte. Next, semen containing a mixture of sperm cells, some with bound antibody or antigen-binding fragment thereof and some without such bound antibody/antigen-binding fragment, are used immediately to inseminate females or to fertilize oocytes in vitro or are processed and frozen using conventional methods known in the art to allow for use to inseminate and/or fertilize upon a later date. In this method the unbound sperm, a population enriched for Y-chromosome bearing sperm, are able to fertilize the oocyte and bias the resulting population of offspring towards males, whereas the bound sperm, a population enriched for X-chromosome bearing sperm, are inhibited.

EXAMPLE 14

Skewing Sex Ratio in Offspring without Separating Sperm

An antibody or antigen-binding fragment thereof derived as described in Examples 2, 8 and/or 11 is conjugated by methods well-known in the art to an inhibitory substance, without intending any limitation including a chemical agent, a pharmaceutical agent, and/or a cytotoxin. The conjugated antibody/antigen-binding fragment is added to a neat or diluted sample of mammalian semen and/or sperm under conditions whereby the antibody/antigen-binding fragment binds to the X-chromosome bearing sperm cells. By the bound inhibitory substance, the antibody/antigen-binding fragment-bound sperm cells are prevented from fertilizing an oocyte. Next, semen containing a mixture of sperm cells, some with bound conjugated antibody/antigen-binding fragment thereof and some without such bound antibody/antigen-binding fragment, are used immediately to inseminate females or fertilize oocytes in vitro or are processed and frozen using conventional methods known in the art to allow for use to inseminate and/or fertilize upon a later date. In this method the unbound sperm, a population enriched for Y-chromosome bearing sperm, are able to fertilize the oocyte and bias the resulting population of offspring towards males, whereas the bound sperm, a population enriched for X-chromosome bearing sperm, are inhibited.

The present disclosure thus responds to a need in the art by providing effective methods for identification of X-chromosome bearing sperm cells, for separation of X-chromosome and Y-chromosome bearing sperm cells, and/or for skewing a ratio of mixed X-/Y-chromosome bearing sperm cells in favor of X-chromosome bearing or Y-chromosome bearing sperm cells. Advantageously, the methods are substantially non-invasive, are reproducible, and provide a viable X-chromosome skewed sperm cell population suitable for subsequent commercial artificial insemination procedures.

In turn, the described methods readily admit of scaling up to commercial scale, such as for sorting large quantities of semen to provide sperm cells tailored for a male or female-skewed sex ratio for artificial insemination purposes, or for providing a sample of semen or sperm cells including a mixed population of X-chromosome bearing and Y-chromosome bearing sperm cells that, by binding of antibody or antigen-binding fragment thereof according to the present disclosure, include X-chromosome bearing sperm cells that are prevented from fertilizing oocytes.

While the terms used herein are believed to be well-understood by one of ordinary skill in the art, definitions are set forth to facilitate explanation of certain of the presently-disclosed subject matter.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter. With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, S, C, and/or O" includes A, S, C, and O individually, but also includes any and all combinations and subcombinations of A, S, C, and O.

The term "antibody" (Ab) as used herein includes monoclonal antibodies, polyclonal antibodies, multispecific antibodies and antibody fragments, as long as they exhibit the desired biological activity. The term "polyclonal antibody" as used herein refers to an antibody obtained from a population of heterogeneous antibodies, i.e., they are secreted by different B cell lineages within the body. The term "monoclonal antibody" as used herein refers to an antibody obtained from a population of substantially homogeneous antibodies, i.e., the individual antibodies that make up the population are identical except for possible naturally occurring mutations. Monoclonal antibodies are highly specific, being directed against a single antigenic site.

The term "antibody" (Ab) as used herein also includes antibody fragments. An "antibody fragment" is a portion of an intact antibody, preferably the antigen binding or variable region of the intact antibody. Examples of antibody fragments include but are not limited to: Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

The term "sex ratio" as used herein refers to the ratio of males to females in a mammalian population. It may also include the prediction of sex ratio in a particular population.

The term "semen" as used herein refers to the fluid and sperm cells contained therein in mammals. Semen as used herein includes neat and diluted semen.

The foregoing description of preferred embodiments has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the disclosed subject matter and its practical application to thereby enable one of ordinary skill in the art to utilize the invention in various embodiments and with various modifications as are suited to the particular use contemplated. All such modifications and variations are within the scope of the invention as determined by the claims when interpreted in accordance with the breadth to which they are fairly, legally and equitably entitled.

REFERENCES

Burry, R. W. (2011), Journal of Histochemistry and Cytochemistry 59: 6-12.
L. A. Johnson (1992), J. Anim. Sci. 70:8-18.
L. A. Johnson (1995), Reprod Fertil Dev. 7(4):893-903.
J. L. Lush (1925), J. Agric. Res. 30:893.
Perret et al. (1990), Genomics 6: 482-90.
Rens et al. (2001), Reproduction 121: 541-6.
G. E. Seidel (2012), J Reprod Dev. 58(5):505-9.

What is claimed:

1. A purified antibody that binds selectively to a mammalian X-chromosome-bearing sperm cell peptide sequence selected from the group consisting of SEQ ID NOs:4 and 9-16, or a sequence having at least 85% homology thereto, the antibody deposited under American Type Culture Collection (ATCC) accession numbers PTA-125897 and/or PTA-125898.

2. A composition for skewing a sex ratio in non-human mammalian offspring by an artificial insemination procedure, comprising:
   a mixed population of mammalian sperm cells including X-chromosome-bearing sperm cells and Y-chromosome-bearing sperm cells; and
   a purified antibody according to claim 1, or an antigen-binding fragment thereof.

3. The composition of claim 2, further wherein the antibody or antigen-binding fragment thereof binds selectively to at least one antigenic sequence selected from the group consisting of SEQ ID NO: 1, SEQ ID NO: 2, and SEQ ID NO: 3.

4. The composition of claim 2, wherein the antibody or antigen-binding fragment thereof is conjugated to an inhibitory substance that prevents the bound sperm cells from fertilizing an oocyte.

5. The composition of claim 4, wherein the inhibitory substance is selected from the group consisting of a chemical agent, a pharmaceutical agent, and a cytotoxin.

6. A method for skewing a sex ratio in non-human mammalian offspring via artificial insemination, comprising:
   obtaining a sample of mammalian semen having a population of sperm cells including X-chromosome-bearing sperm cells and Y-chromosome-bearing sperm cells; and
   contacting a neat or a diluted portion of the sample of semen and/or the population of sperm cells with an antibody according to claim 1 or an antigen-binding fragment thereof to provide a mixed population of sperm cells including a portion of sperm cells having the antibody or antigen-binding fragment bound thereto.

7. The method of claim 6, wherein the antibody is derived by immunization of a host by an antigenic peptide composition comprising a natural or a synthetic antigenic amino acid sequence selected from the group of sequences consisting of SEQ ID NOs: 4 and 9-16, or an antigenic sequence having at least 85% homology thereto.

8. The method of claim 7, wherein the natural or synthetic antigenic amino acid sequence includes one or more sequences selected from the group consisting of SEQ ID NO: 1, SEQ ID NO: 2, and SEQ ID NO: 3.

9. The method of claim 6, further including fertilizing a non-human oocyte with at least a portion of the mixed population of sperm cells.

10. The method of claim 9, further including separating sperm cells having the antibody or antigen-binding fragment thereof bound thereto from other sperm cells of the mixed population of sperm cells prior to the step of fertilizing to provide a Y-chromosome-enriched population of sperm cells for the step of fertilizing the oocyte.

11. The method of claim 10, wherein the separating is performed by one or more of fluorescent-activated cell sorting, magnetic cell sorting, adherence to antibody-coated tubes, adherence to antibody-coated plates, adherence to antibody-coated beads, and combinations thereof.

12. The method of claim 6, including obtaining the sample of semen from a mammal selected from the group consisting of bovines, equines, ovines, Cervidae, camelids, and porcines.

13. The method of claim 12, wherein the mammal is one of Bos Taurus and Bos indicus, or a cross-breeding thereof.

* * * * *

UNITED STATES PATENT AND TRADEMARK OFFICE
CERTIFICATE OF CORRECTION

| | | |
|---|---|---|
| PATENT NO. | : 11,760,793 B2 | Page 1 of 1 |
| APPLICATION NO. | : 17/126677 | |
| DATED | : September 19, 2023 | |
| INVENTOR(S) | : J. Lannett Edwards, Louisa A. Rispoli and F. Neal Schrick | |

It is certified that error appears in the above-identified patent and that said Letters Patent is hereby corrected as shown below:

On the Title Page

Column 1, insert:
--Related U.S. Application Data
U.S. Provisional App. Ser. No. 61/942,020, filed February 19, 2014
U.S. Provisional App. Ser. No. 62/065,797, filed October 20, 2014
U.S. Patent App. Ser. No. 14/626,401, filed February 15, 2015--

Signed and Sealed this
Nineteenth Day of December, 2023

Katherine Kelly Vidal
*Director of the United States Patent and Trademark Office*